United States Patent [19]
Kojima et al.

[11] Patent Number: 6,166,091
[45] Date of Patent: Dec. 26, 2000

[54] 2,3,4-TRIHYDROXYCYCLOPENTANONE

[75] Inventors: Kaoru Kojima, Hirosaki; Katsushige Ikai, Otsu; Tatsuji Enoki, Otsu; Nobuto Koyama, Otsu; Ikunoshin Kato, Otsu, all of Japan

[73] Assignee: Takara Shuzo Co., Ltd., Kyoto, Japan

[21] Appl. No.: 09/402,086

[22] PCT Filed: Jun. 1, 1998

[86] PCT No.: PCT/JP98/02425

§ 371 Date: Sep. 29, 1999

§ 102(e) Date: Sep. 29, 1999

[87] PCT Pub. No.: WO98/56745

PCT Pub. Date: Dec. 17, 1998

[30] Foreign Application Priority Data

Jun. 13, 1997 [JP] Japan ..................................... 9-171193
Jul. 15, 1997 [JP] Japan ..................................... 9-203903

[51] Int. Cl.[7] ........................ A61K 31/122; C07C 49/297
[52] U.S. Cl. ......................... 514/690; 514/729; 426/592; 426/658; 568/338; 568/379; 568/361; 568/838
[58] Field of Search ..................................... 568/379, 338, 568/838, 361; 514/690, 729; 426/592, 658

[56] References Cited

U.S. PATENT DOCUMENTS 3,982,996  9/1976  Daum et al. .............................. 195/29

FOREIGN PATENT DOCUMENTS 61-1636   1/1986  Japan .
5-238978  9/1993  Japan .

OTHER PUBLICATIONS

J. Elliott et al., *Tetrahedron Letters*, 24(9), 965–968 (1983).

*Primary Examiner*—Sreeni Padmanabhan
*Attorney, Agent, or Firm*—Wenderoth, Lind & Ponack, L.L.P.

[57] ABSTRACT

2,3,4-trihydroxycyclopentanone represented by the following formula [I], its optically active substance or salt thereof.

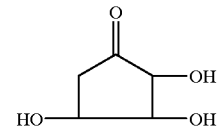

[I]

12 Claims, 14 Drawing Sheets

2,3,4-TRIHYDROXYCYCLOPENTANONE

This is the U.S. National stage Application of PCT/JP98/02425 filed Jun. 01, 1998 now WO98/56745 published Dec. 17, 1998.

TECHNICAL FIELD

The present invention relates to the hydroxycyclopentanone compounds useful in the field of pharmaceutical agents, food or beverage having a physiological activity such as anticancer action and also relates to manufacturing methods and uses thereof.

PRIOR ART

Pharmaceuticals which have been used in clinical therapy include many agents such as anticancer agents, antibiotic substances, immunopotentiators, immunomodulators, etc. (such as alkylating agents, antimetabolites and plant alkaloids) but it is hardly said that such a drug therapy has been completely established already.

Among those agents, prostaglandin A and J having a cyclopentenone ring among the prostaglandins derived from natural substances have been reported to have a possibility of being used as highly-safe anticancer agents due to their inhibition of DNA synthesis and various derivatives of them have been synthesized (refer to the Japanese Laid-Open Patent Publication Sho-62/96438).

PROBLEMS TO BE SOLVED BY THE INVENTION

An object of the present invention is to develop highly-safe cyclopentanone compounds having physiological actions such as an anticancer action and to offer manufacturing methods for said compounds, pharmaceutical agents and food or beverage containing said compounds.

MEANS TO SOLVE THE PROBLEMS

The present inventors have found that a compound which is 2,3,4-trihydroxy-2-cyclopentanone (hereinafter, just referred to as "hydroxycyclopentanone") represented by a formula [I] is produced in a heat-treated products of at least one substance selected from uronic acid, uronic acid derivative(s), a saccharide compound containing uronic acid and/or uronic acid derivative(s) therein and a substance which contains a saccharide compound containing uronic acid and/or uronic acid derivative(s) therein and that said compound which is isolated from the heat-treated products has a physiological activity such as a anticancer action whereupon the present invention has been achieved.

Now the present invention will be summarized to be as follows. Thus, the first feature of the present invention relates to 2,3,4-trihydroxycyclopentanone represented by the following formula [I], its optically active substance or salt thereof.

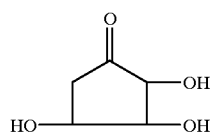

[I]

The second feature of the present invention relates to a method for the manufacture of 2,3,4-trihydroxycyclopentanone represented by the formula [I], its optically active substance or salt thereof characterized in comprising the following steps.

(A): a step where at least one substance selected from the following (a), (b) and (c) is heated to produce 2,3,4-trihydroxycyclopentanone
  (a) uronic acid or uronic acid derivative(s)
  (b) a saccharide compound containing uronic acid and/or uronic acid derivative(s)
  (c) a substance which contains a saccharide compound containing uronic acid and/or uronic acid derivative(s)

(B): a step where 2,3,4-trihydroxycyclopentanone is isolated from the heat-treated product if necessary.

The third feature of the present invention relates to a method for the manufacture of 2,3,4-trihydroxycyclopentanone represented by the formula [I], its optically active substance or salt thereof characterized in comprising a step where 4,5-dihtydroxy-2-cyclopenten-1-one represented by the following formula [II] is converted to 2,3,4-trihydroxycyclopentanone represented by the formula [I].

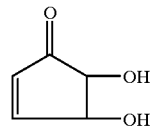

[II]

The fourth feature of the present invention relates to a pharmaceutical agent containing at least one compound selected from 2,3,4-trihydroxycyclopentanone, its optically active substance or salt thereof according to the first feature of the present invention as an effective component.

The fifth feature of the present invention relates to food or beverage containing at least one compound selected from 2,3,4-trihydroxycyclopentanone, its optically active substance or salt thereof according to the first feature of the present invention.

PREFERRED EMBODIMENTS OF THE INVENTION

Figure 1:
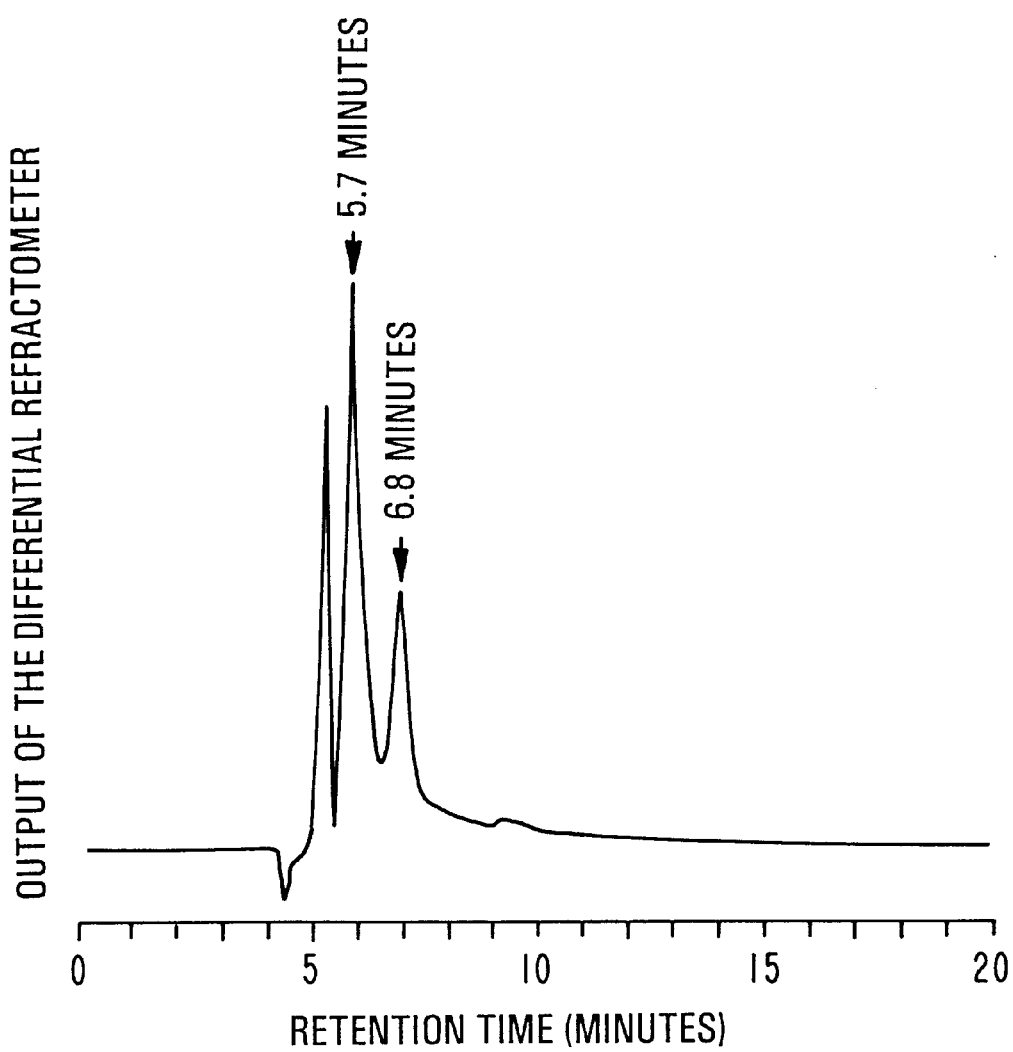
FIG. 1 shows the relation between the retention time and the output of the differential refractometer.

The present invention will now be more specifically illustrated as hereinafter.

In the present invention, there is no particular limitation for uronic acid, uronic acid derivative(s), a saccharide compound containing uronic acid and/or uronic acid derivative(s) and a substance which contains a saccharide compound containing uronic acid and/or uronic acid derivative(s) so far as the hydroxycyclopentanone is produced in the heat-treated products thereof.

It is now possible in accordance with the present invention that an appropriate amount of the physiologically active hydroxycyclopentanone, its optically active substance or salt thereof is contained in food or beverage. As a result of anticancer action, etc. of those compounds, the food or beverage of the present invention is quite useful as anticancer food or as anticancer beverage.

In addition, the present invention offers pharmaceutical agents containing the hydroxycyclopentanone, its optically active substance or salt thereof and said pharmaceutical agents are useful as therapeutic or preventive agents for cancer.

The hydroxycyclopentanone used in the present invention can be produced by heating a substance selected from (a) uronic acid or uronic acid derivative(s); (b) a saccharide compound which contains uronic acid and/or uronic acid derivative(s); and (c) a substance containing a saccharide compound which contains uronic acid and/or uronic acid derivative(s). Accordingly, it is also possible to prepare the hydroxycyclopentanone of the present invention by heating (a), (b) or (c) which is produced from a material containing neither (a), (b) nor (c) by physical, chemical, enzymatic or other means.

It is also possible in the present invention to use the heat-treated products containing the hydroxycyclopentanone or the partially-purified hydroxycyclopentanone or purified hydroxycyclopentanone obtained from the above heat-treated products.

Uronic acid is sometimes called glycuronic acid and is a general name for hydroxyaldehyde carboxylic acids in which an aldehyde group on aldose remains as it is while only a primary alcohol group at another end is oxidized to a carboxyl group. It is present in nature as a constituting component for various polysaccharides of animals and plants. Examples of the polysaccharide containing uronic acid are pectin, pectic acid, alginic acid, hyaluronic acid, heparin, heparan sulfate, fucoidan, chondroitin sulfate, chondroitin, dermatan sulfate, etc. and they have been known to exhibit various physiological functions.

There is no particular limitation for the uronic acid used in the present invention. Thus, examples of the uronic acid are galacturonic acid, glucuronic acid, guluronic acid, mannuronic acid and iduronic acid while examples of the uronic acid derivative(s) are lactones, esters, amides, salts, etc. of the above-mentioned ones and any substance which produces the hydroxycyclopentanone on heating is covered by the derivative of the present invention. Examples of the uronic acid lactone are glucurono-6,3-lactone (hereinafter, abbreviated as glucuronclactone), mannurono-6,3-lactone and idurono-6,3-lactone. Examples of the uronic acid ester are methyl, ethyl, propylene glycol and carboxymethyl uronates which can be manufactured from uronic acid. Uronic acid amide can be manufactured by amidation of uronic acid. Salts of them can be manufactured by common methods.

There is no particular limitation for the saccharide compound containing uronic acid and/or uronic acid derivative(s) in this specification and the examples applicable are pectin, pectic acid, alginic acid, hyaluronic acid, heparin, heparan sulfate, fucoidan, chondroitin sulfate, chondroitin and dermatan sulfate including decomposed products, derivatives of the decomposed products and salts of the decomposed products thereof which are chemically, enzymatically or physically-treated products thereof.

In the above-mentioned chemical treatment, the starting compound is, for example, treated at room temperature to 200° C. for several seconds to several hours or, preferably, at 50–130° C. for several seconds to 60 minutes. When said treatment is conducted under acidic condition, glycoside bond is hydrolyzed and, in the case of pectin, a decomposed product containing galacturonic acid and/or galacturonic acid ester is resulted. Or, for example, when treated at pH 6.8, 95° C. for several minutes to several tens minutes, a beta-elimination takes place to give a saccharide compound having unsaturated uronic acid and/or unsaturated uronic acid ester in which an absorbance at around 235 nm is increased. The saccharide compound of the present invention covers a saccharide compound containing unsaturated uronic acid and/or unsaturated uronic acid ester at a non-reducing end prepared by a beta-elimination of a polysaccharide compound containing uronic acid and/or uronic acid ester.

An example of the above-mentioned enzymatic treatment is a known decomposition method in which the starting saccharide compound containing uronic acid and/or uronic acid ester is decomposed by a hydrolase such as pectinase and hyaluronidase for the saccharide containing uronic acid and/or uronic acid ester. Another example is a known decomposition method in which the saccharide containing uronic acid and/or uronic acid ester is decomposed by a lyase for the saccharide containing uronic acid and/or uronic acid ester. For example, in the case of pectin or pectic acid, a decomposition is conducted by a known pectin lyase (EC 4.2.2.10), pectate lyase (EC 4.2.2.2) or exopolygalact-uronic acid lyase (EC 4.2.2.9) to give a saccharide compound having 4-deoxy-L-threo-hex-4-enopyranosyl uronate or methyl ester thereof at a non-reducing end. In the case of hyaluronic acid, a hyaluronate lyase (EC 4.2.2.1) is used while, in the case of alginic acid, an alginate lyase (EC 4.2.2.3) is used. Incidentally, in the case of alginic acid, a saccharide compound having 4-deoxy-L-erythro-hex-4-enopyranosyl uronate at its non-reducing end is obtained. The enzymatically decomposed products having 4-deoxy-L-threo-hex-4-enopyranosyl uronate, 4-dexoy-L-erythro-hex-4-enopyranosyl uronate or methyl ester thereof at the non-reducing end prepared as such are covered by the saccharide compound of the present invention as well.

Examples of the above-mentioned physical treatment are the treatment of the starting saccharide compound with near infrared ray, infrared ray, microwave, ultrasonic wave, etc. Thus, for example, pectin and/or pectic acid are/is placed in a neutral (in terms of pH) or an alkaline solution and subjected to an ultrasonic wave for applying a vibrational energy at an appropriate temperature of not lower than room temperature under an appropriate reductive operation, for example, in the presence of ascorbic acid for not shorter than one second or, preferably, from five seconds to one hour. Besides the ultrasonic wave, it is also effective to irradiate with microwave, near infrared ray, infrared ray, etc. or a combination thereof. The irradiation may be conducted either continuously or intermittently.

In the present invention, there is no particular limitation for the substance which contains a saccharide compound containing uronic acid and/or uronic acid derivative(s) so far as said substance contains a saccharide compound containing the above-mentioned uronic acid and/or uronic acid derivative(s). Examples of the substance which contains the saccharide compound containing uronic acid or uronic acid derivative(s) are as follows. Thus, fruits, vegetables, leaves, seeds, etc. of dicotyledonous plants such as apple, citrus fruits (e.g., mandarin orange and lemon), banana, nappa cabbage, cabbage, lettuce, perilla, pumpkin, celery, burdock, echalote, broccoli, green pepper, spinach, onion, carrot, leaves of carrot, leaves of daikon (Japanese radish), tea leaves, sesame, beans, potato, etc.; cereals of monocotyledonous plants such as wheat and rice; algae such as brown algae (e.g., sea tangle and wakame seaweed), red algae, green algae and unicellular green algae; microorganisms such as Basidiomycetes (e.g., Lyophyllum ulmarium, Lyophyllum decastes, Pholiota nameko, Cortinellus shiitake, Flammulina verutipes, Agaricus ostreatus and Pasalliota campestris), Ascomycetes (e.g., Cordyceps militaris and other Cordyceps sp.), yeasts, filamentous fungi (e.g., Aspergillus sp.) and bacteria (e.g., Bacillus natto and lactic acid bacteria); and animals such as vertebrate animals and invertebrate animals including skin of pigs, skin of cows, cartilage of shark, cartilage of whale, etc. In the present invention, a substance which contains a saccharide compound containing uronic acid and/or uronic acid derivatives derived from the above-mentioned plants, microorganisms or animals may be used.

Moreover, in the present invention, the following agricultural and fishery products or processed food products as they are or after drying/crushing may be used as the substance which contains a saccharide compound containing uronic acid and/or uronic acid derivative(s). They are rind of a fruit, strained lees of a fruit (such as those of apple and mandarin orange), strained lees of a vegetable, strained lees of cereals (such as those obtained in the preparation of sake [Japanese rice wine], beer, shochu [Japanese distilled spirits] and whiskey), strained lees of beans (such as okara [Japanese bean-curd refuse]) and strained lees of sea algae, etc.

The substance which contains a saccharide compound containing uronic acid and/or uronic acid derivative(s) used in the present invention may be used as it is or may be subjected to any of the conventional processes such as boiling, baking, dry-roasting, roasting, decocting, steaming, frying, deep-frying, etc. as a pretreatment.

Moreover, in the present invention, the substance which contains a saccharide compound containing uronic acid and/or uronic acid derivative(s) may be subjected to the above-mentioned chemical, enzymatic (including fermentational one using microorganisms) or physical pretreatment and the resulting substance treated as such or purified substance prepared from said resulting substance may be used as well.

The polysaccharides which are saccharide compounds containing uronic acid and/or uronic acid derivative(s) can be manufactured by known chemical, enzymatic or physical methods. In the case of pectin for example, a high-molecular weight polysaccharide extracted from, for example, rind of citrus fruits or apple may be used. Materials for the manufacture of pectin on an industrial scale are fruits and, in addition to strained lees (mostly comprising endocarp) after preparing juice of citrus fruits such as lemon and lime, the strained lees after preparation of apple juice is used as well. Such strained lees mostly contain an insoluble protopectin and it is solubilized (extracted) during the course of manufacture to prepare pectin. Solubilization can be conducted by extracting with an acidic warm to hot water and, when the conditions such as temperature, pH and time in extracting are properly controlled depending upon the type of the starting material, it is possible to manufacture pectin having predetermined molecular weight and degree of esterification in a high yield. The extract is purified by means of centrifugation or filtration and concentrated and alcohol is added thereto whereupon pectin can be precipitated and recovered. The recovered precipitate is dried and crushed to prepare a dry pectin.

The main structure of pectin is a partially methylated galacturonic acid polymer. The carboxyl group is either methylesterified, left as a free acid or made into a salt such as ammonium salt, potassium salt or sodium salt. Depending upon the degree of methylesterification (DM; ratio of methoxyl groups to total carboxyl groups), pectin is classified into an HM pectin having a high DM and an LM pectin having a low DM ["Handbook of Materials for Developing New Food Products" edited by Satoshi Yoshidumi, et al., published by K. K. Korin, pages 114–119 (1991)] and, in the present invention, pectin which is commercially available as a food additive ["Handbook of Natural Products", edited by Akio Toyama, published by Shokuhin To Kagakusha, 12th Edition, page 138 (1993)], commercially available HM pectin and LM pectin, etc. [refer to the above-mentioned "Handbook of Materials for Developing New Food Products"] may be used.

Uronic acid, uronic acid derivatives, oligosaccharides, etc. which are synthesized by a synthetic means may be used in the present invention as well.

The heat-treated substance used in the present invention may be manufactured using a substance selected from (a) uronic acid or uronic acid derivatives(s), (b) a saccharide compound containing uronic acid and/or uronic acid derivative(s) and (c) a substance which contains a saccharide compound containing uronic acid and/or uronic acid derivative(s) as a starting material.

There is no particular limitation for the method of the heating treatment in the manufacture of the heat-treated substance containing hydroxycyclopentanone used in the present invention so far as the hydroxycyclopentanone of the present invention can be produced. Thus, for example, uronic acid, uronic acid derivative(s), a saccharide compound containing uronic acid and/or uronic acid derivative (s) or a substance which contains a saccharide compound containing uronic acid and/or uronic acid derivative(s) is heated at 60–350° C. for several seconds to several days or, preferably, at 80–150° C. for several minutes to several days. In the case of pectin, a heat-treated substance containing the hydroxycyclopentanone can be obtained by heating, for example, at 80–150° C. for several minutes to several days. Alternatively, when uronic acid, uronic acid lactone or uronic acid ester is heated at 60–150° C. for several minutes to several days, a desired heat-treated substance containing the hydroxycyclopentanone can be obtained.

There is no particular limitation for the pH upon the heating treatment and it is preferred to conduct under neutral to acidic conditions. The pH during the heating treatment may be adjusted depending upon the type of the materials used.

There is no particular limitation for the concentrations of the materials upon the heating treatment so far as the concentrations are within such a range that the hydroxycyclopentanone can be produced and they may be set by taking operability, yield, etc. into consideration. The heating treatment in the present invention may be either wet heating or dry heating although, in view of the productive efficiency of the hydroxycyclopentanone of the present invention, a wet heating is preferred. In the case of a wet heating, any of wet heating methods such as heating with steam, heating with steam under high pressure, heating under high pressure, etc. may be used while, in the case of a dry heating, any of dry heating methods such as a direct heating using dry and hot air and an indirect heating from a heat source through a partition may be used. Examples of the direct heating are a dry heating by an air stream and a dry heating by means of spraying while those of the indirect heating are a dry heating by means of a drum, etc.

The hydroxycyclopentanone in the heat-treated product used in the present invention can be purified or isolated using the cancer cell growth inhibition, etc. as an index. With regard to a purifying or isolating means, any of known purifying and isolating means such as chemical methods and physical methods may be used. Thus, purifying methods which have been known already such as gel filtration, fractionating using a molecular weight fractionating membrane, extraction with solvent, fractional distillation, various chromatographic methods using ion-exchange resin or of a normal phase or a reversed phase, etc. may be jointly used whereby the hydroxycyclopentanone produced in the heat-treated substance can be collected.

For example, an aqueous solution of glucuronolactone is heated and the heated solution is subjected to anion exchange column chromatography, synthetic adsorbent column chromatography and silica gel column chromatography successively whereupon hydroxycyclopentanone can be purified.

Alternatively, hydroxycyclopentanone of the present invention can be manufactured using 4,5-dihydroxy-2-cyclopenten-1-one (hereinafter, just referred to as "cyclopentenone") represented by the following formula [II] as a starting material.

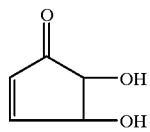

[II]

For example, hydroxycyclopentanone is produced by dissolving cyclopentenone in water or in a water-containing solvent. There is no particular limitation for the condition for production of hydroxycyclopentanone of the present invention so far as it is a condition whereby hydroxycyclopentanone can be produced.

Amount of the produced hydroxycyclopentanone can be measured by an HPLC using a column of normal phase or reversed phase, gas chromatography, thin layer chromatography, paper chromatography, nuclear magnetic resonance, etc.

With regard to a method for purifying hydroxycyclopentanone, any of known methods such as chemical methods and physical methods may be used. Thus, purifying methods which have been known already such as gel filtration, fractionating using a molecular weight fractionating membrane, extraction with solvent, fractional distillation, various chromatographic methods using ion-exchange resin or of a normal phase or a reversed phase, etc. may be jointly used whereby the hydroxycyclopentanone or its optically active substance in the heat-treated substance can be purified or isolated.

For example, when an aqueous solution of the cyclopentenone is stored at 4° C. for 30 days, about 30% of the cyclopentenone changes to hydroxycyclopentanone.

Structure of the isolated hydroxycyclopentanone can be determined by known methods such as mass spectrometry, nuclear magnetic resonance, infrared absorption spectrum, ultraviolet absorption, etc.

Hydroxycyclopentanone of the present invention and cyclopentenone are changed from one to another in an aqueous solution and they are in an equilibrated relation. Hydroxycyclopentanone is produced from the isolated cyclopentenone as mentioned above and, on the other hand, a part of hydroxycyclopentanone changes to cyclopentenone when the isolated hydroxycyclopentanone is allowed to stand as an aqueous solution.

The method for the manufacture of the cyclopentenone, which is represented by the formula [II], used in the present invention can be manufactured by a chemical synthetic method [Carbohydrate Research, volume 247, pages 217–222 (1993); Helvetica Chimica Acta, volume 55, pages 2838–2844 (1972)]. Further, the cyclopentenone is a compound which is produced in the heat-treated substance of at least one selected from uronic acid, uronic acid derivative (s), a saccharide compound containing uronic acid and/or uronic acid derivatives and a substance which contains a saccharide compound containing uronic acid and/or uronic acid derivative(s) and purified product thereof may be used in the present invention as well.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated and the cyclopentenone is extracted with chloroform from the concentrate whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP 370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu)

FAB-MS m/z 115 [M+H]$^+$

Glycerol was used as matrix.

$^1$H-NMR (CDCl$_3$); δ 4.20 (1H, d, J=2.4 Hz, 5-H), 4.83 (1H, m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1.3, water) IR (KEr method): absorptions were noted at 3400, 1715, 1630, 1115, 1060, 1025 cm$^{-1}$.

UV: $\lambda_{max}$ 215 nm (water)

It is possible to prepare an optically active hydroxycyclopentanone when the isolated hydroxycyclopentanone is subjected to an optical resolution. An optically active cyclopentenone can be prepared similarly.

Separation of the optically active substances can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, that of a polysaccharide, that of a polysaccharide derivative, protein stationary phase, polymethacrylic acid ester stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to the hydroxycyclopentanone or its optically active substance, salts which are acceptable as pharmaceuticals are exemplified and they may be prepared by converting by means of known methods.

The hydroxycyclopentanone of the present invention, its optically active substance or salt thereof has physiological activities s such as anticancer activity, activity of growth inhibition n of cancer cells, apoptosis-inducing activity, activity of topoisomerase II inhibition, induction activity of the cancer cell differentiation, antirheumatic activity, activity of chronic articular rheumatism inhibition, activity of inducing the Fas antigen production, antibacterial activity, antiviral activity, activity of improving the hepatic function, activity of inducing the heat shock protein, normalizing activity of t he blood components, enhancer activity of the cancer immunity, anti-inflammation activity, inhibition activity of tumor necrosis factor expression, inhibition activity of nitrogen monoxide production and immunomodulating activity such as inhibition activity of delayed type hypersensitivity, inhibition activity of lymphocyte transformation, inhibition activity of mixed lymphocyte reaction, inhibition activity of IgE production and inhibition activity of carrageenan edema and, due to those activities, pharmaceutical agent containing as an effective component at least o one compound which is selected from hydroxycyclopentanone, its optically active substance and salt thereof is useful as, for example, a pharmaceutical agent acting biophylaxic mechanism such as pharmaceutical preparation acting on an antibody production mechanism, anti-inflammatory agent, antiallergic agent, antirheumatic agent and interferon inducer, a pharmaceutical agent acting the saccharide metabolism such as remedy for diabetes mellitus, a pharmaceutical agent acting the pathogenic organisms such as antibacterial agent and antiviral agent, etc. Accordingly, the pharmaceutical agent obtained by the present invention is quite useful as a pharmaceutical agent for the diseases which show sensitivity to the hydroxycyclopentanone of the present invention, its optically active substance or salt thereof, i.e. as a pharmaceutical agent for therapy or prevention of, for example, cancer, viral diseases, rheumatism, diabetes mellitus, allergy, autoimmune diseases, inflammation, etc.

The hydroxycyclopentanone, its optically active substance or salt thereof has a cell growth suppressing action and anticancer action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. Thus, anticancer agent containing at least one of the compound selected from the hydroxycyclopentanone, its optically active substance or salt thereof as an effective component can be manufactured. Further, those compounds have an apoptosis-inducing action to those cancer cells and a topoisomerase II inhibiting action of cancer cells too. Mechanism of the action for inhibiting the cancer cell growth of the hydroxycyclopentanone, its optically active substance or salt thereof does not limit the scope of the present invention at all and, for example, a topoisomerase II inhibiting action and an apoptosis inducing action to cancer cells are covered by anticancer activity in the present invention as well.

Generally, the hydroxycyclopentanone, its optically active substance or salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The anticancer agent of the present invention is administered by an appropriate route depending upon the form of the preparation. There is no particular limitation for the method of administration as well and it may be administered by oral use, external use and injection. Preparations for injection are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated with and it is not constant but, usually, the amount of the hydroxycyclopentanone, its optically active substance or salt thereof contained in the preparation is from 10 pg to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

Pharmaceutical agents acting on a biophylaxic mechanism such as pharmaceutical preparation acting on an antibody production mechanism, antiinflammatory agent, antiallergic agent, antirheumatic agent and interferon inducer, a pharmaceutical agent acting on a saccharide metabolism such as remedy for diabetes mellitus, and a pharmaceutical agent acting on a pathogenic organism such as antibacterial agent, antiviral agent, apoptosis inducer, etc. containing at least one compound selected from hydroxycyclopentanone, its optically active substance or salt thereof as an effective component may be made into pharmaceutical preparations by a method similar to that for anticancer agents and may be administered by a method and at a dose similar to those for anticancer agents.

Hydroxycyclopentanone is in an equilibrated relation with cyclopentenone in an aqueous solution and it is believed that hydroxycyclopentanone which is converted from cyclopentenone in vivo also achieves an effect as a pharmaceutical agent. Accordingly, the use of cyclopentenone, its optically active substance or salt thereof with an object of production of hydroxycyclopentanone in vivo is covered by the present invention as well.

Hydroxycyclopentanone or its optically active substance according to the present invention has various physiological activities such as an action of suppressing the growth of cancer cells and food or beverage where at least one of hydroxycyclopentanone, its optically active substance or salt thereof according to the present invention is contained therein, diluted therein or added thereto is useful as a functional food or beverage having, for example, an anticancer action.

Incidentally, in the manufacture of the food or beverage of the present invention, it is possible to use the heat-treated product containing hydroxycyclopentanone, partially purified hydroxycyclopentanone from said heat-treated product, pure hydroxycyclopentanone and/or its optically active substance.

There is no particular limitation for food or beverage of the present invention which at least one compound selected from hydroxycyclopentanone, its optically active substance or salt thereof is contained therein, diluted therein or added thereto and its examples are processed agricultural and forest products, processed livestock products, processed fishery products, etc. such as processed cereals (for example, processed wheat flour, processed starch, processed premix, noodles, macaroni, bread, bean paste, soba [buckwheat noodles], fu [wheat-gluten bread], biifun [Chinese noodles made of rice flour], harusame [sticks of bean jelly] and packed rice cake), processed fat/oil (for example, plastic fat/oil, oil for deep frying, salad oil, mayonnaise and dressing), processed soybeans (for example, tofu [soybean curd], miso [soybean paste] and natto [fermented soybeans]), processed meat products (for example, ham, bacon, pressed ham and sausage), fishery products (frozen fish paste, kamabDko [boiled fish paste], chikuwa [a kind of fish paste product], hampen [cake of pounded fish], satsuma-age [fried fish balls], tsumire [steamed fish balls], suji [boiled raw fish paste], fish meat ham, sausage, dried bonito, processed fish egg products, canned fishery products and tsukudani [food boiled down in soy sauce]), milk product (for example, crude milk, cream, yoghurt, butter, cheese, condensed milk, powdery milk and ice cream), processed vegetable and fruit products (for example, pastes, jams, pickles, fruit beverages, vegetable beverages and mixed beverages), confectioneries (for example, chocolate, biscuit, bun, cake, mochigashi [rice ball cake] and rice crackers), alcoholic beverages (for example, sake [Japanese rice wine], Chinese wines, wine, whisky, shochu [Japanese distilled liquor], vodka, brandy, gin, ram, beer, refreshing alcoholic drinks, fruit wine and liquors), table luxuries (for example, green tea, tea, oolong tea, coffee, refreshment beverage and lactic acid beverage), seasoning (for example, soy sauce, Wooster sauce, vinegar and mirin [sweetened Japanese rice wine]), canned, bottled or bagged food (for example, boiled rice assorted with seasoned beef, kamameshi [boiled rice placed in a small kettle], sekihan [festive red rice], curried rice and other already-cooked food products), semi-dried or concentrated food (for example, liver paste and other spreads, soup for soba and udon [both being typical Japanese noodles] and concentrated soup), dried food (for examples, instant noodles, instant curry, instant coffee, powdery juice, powdery soup, instant soy paste soup, retort food, retort beverage and retort soup), frozen food (for example, frozen sukiyaki, chawanmushi [pot-steamed hotchpotch], kabayaki [grilled eel], hamburg steak, Chinese shao-mai, gyoza [fried dumpling stuffed with minced pork], various sticks and fruit cocktails), solid food products, liquid food products (for example, soup) and spices.

There is no particular limitation for the method of manufacturing the food and beverage of the present invention but cooking, processing and commonly-used manufacturing methods for food and beverage may be applied provided that the hydroxycyclopentanone, its optically active substance or salt thereof having an anticancer action is contained in the resulting food or beverage.

Cooking and processing are to be conducted in such a manner that the compound selected from the hydroxycyclopentanone, its optically active substance or salt thereof is contained in the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s).

Thus, before, during or after cooking/processing, the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s) that contains the compound selected from the hydroxycyclopentanone, its optically active substance or salt thereof may be added or, alternatively, cooked/processed product or a material thereof is added to the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s) that contains the compound selected from the hydroxycyclopentanone, its optically active substance or salt thereof whereby the compound selected from the hydroxycyclopentanone, its optically active substance or salt thereof in said heated-treated substance can be diluted.

Then, in the manufacture of food or beverage, a heating treatment may be conducted during any of the steps whereby the effective amount of the compound selected from hydroxycyclopentanone, its optically active substance or salt thereof may be made to contain in the heat-treated substance or, alternatively, a heat-treated substance which contains the compound selected from hydroxycyclopentanone, its optically active substance or salt thereof may be added thereto. It is also possible that food, beverage or a material thereof is added to a heat-treated substance containing the compound selected from hydroxycyclopentanone, its optically active substance or salt thereof so that the compound selected from hydroxycyclopentanone, its optically active substance or salt thereof in said heat-treated substance may be diluted. Addition may be conducted either at one time or dividedly in several times. Thus, food or beverage showing novel physiological action can be manufactured easily and conveniently. Incidentally, food or beverage containing the compound selected from hydroxycyclopentanone, its optically active substance or salt thereof in the heat-treated substance produced during the manufacture as constituting components after adding (a) uronic acid or uronic acid derivative(s), (b) a saccharide compound containing uronic acid and/or uronic acid derivative(s) and (c) a substance which contains a saccharide compound containing uronic acid and/or uronic acid derivative(s) during the manufacture is also covered by the present invention. In case where any of the steps is applied, food or beverage wherein the compound selected from hydroxycyclopentanone, its optically active substance or salt thereof is contained, added and/or diluted is defined as the food or beverage of the present invention.

Food or beverage where hydroxycyclopentanone derivative produced in food or beverage as a reaction product of hydroxycyclopentanone, its optically active substance or salt thereof with an SH-containing compound such as SH-containing amino acid or its derivative (e.g., cysteine-containing amino acid derivative) is contained therein, added thereto and/or diluted therein is defined as the food or beverage of the present invention as well.

There is no particular limitation for the content of the compound selected from hydroxycyclopentanone, its optically active substance or salt thereof having an anticancer action in the food but the content may be appropriately selected in view of organoleptic property and physiological activity. However, for example, the content of the compound selected from hydroxycyclopentanone, its optically active substance or salt thereof having an anticancer action in the food in 100 parts of food is $10^{-9}$ part or more and, in view of organoleptic property and anticancer action of the food, it is preferably from $10^{-8}$ to 5 parts or, more preferably, from $10^{-7}$ to 2 parts. Anyway, the food in a physiologically effective amount may be taken.

There is no particular limitation for the content of the hydroxycyclopentanone, its optically active substance or salt thereof having an anticancer action in the beverage but the content may be appropriately selected in view of organoleptic property and physiological activity. However, for example, the content of the compound selected from the hydroxycyclopentanone, its optically active substance or salt thereof having an anticancer action in the beverage in 100 parts of beverage is $10^{-9}$ part or more and, in view of organoleptic property and anticancer action of the beverage, it is preferably from $10^{-8}$ to 5 parts or, more preferably, from $10^{-7}$ to 2 parts. Anyway, the beverage in a physiologically effective amount may be taken. Incidentally, the term "part (s)" used in the present specification stands for "part(s) by weight".

There is no particular limitation for the shape of the food or beverage of the present invention so far as the hydroxycyclopentanone, its optically active substance or salt thereof having an anticancer action is contained therein, added thereto and/or diluted thereby. Thus, the shape includes orally takable ones such as tablets, granules, capsules, gel and sol.

The food or beverage of the present invention contains a physiologically active compound selected from hydroxycyclopentanone, its optically active substance or salt thereof and, due to various physiological actions of hydroxycyclopentanone, its optically active substance or salt thereof such as anticancer action, antibacterial action, apoptosis inducing action, antiviral action and action of improving the hepatic function, it is a healthy food or beverage showing effect of prevention of carcinogenesis, effect of suppression of cancer, effect of prevention and therapy of viral diseases, effect of prevention of Alzheimer's disease and effect of improvement of hepatic functions and is useful for maintenance of homeostasis of living body, particularly for keeping the good health of stomach and intestine. In addition, due to its antibacterial action, it is a food and beverage having a very good preservability.

Incidentally, no toxicity was noted by oral administration of 100 mg/kg of hydroxycyclopentanone, its optically active substance or salt thereof of the present invention to mice.

EXAMPLES

The present invention will be further illustrated by way of the following examples although the present invention is never limited to those examples. Incidentally, "%" used in the examples stands for "% by weight".

Example 1.

(1) D-Glucuroic acid (G 5269; manufactured by Sigma) (10 g) was dissolved ed i n 1 liter of water, heated at 121° C. for four hours and concentrated in vacuo to about 10 ml. This was mixed with 40 ml of an upper layer of a 3:2:2 mixture of butyl acetate, acetic acid and water and centrifuged and the resulting supernatant liquid was concentrated in vacuo to about 10 ml.

The above extract was applied to silica gel (BW-300SP; 2×28 cm; manufactured by Fuji Silycia Chemical) for a column chromatography and separated using an upper layer of a 3:2:2 mixture of butyl acetate, acetic acid and water as an eluate at the flow rate of about 5 ml/minute with a pressure of 0.2 kg /cm² using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a PALPACK type S column and, when a detection was conducted by an ultraviolet absorption of 215 nm, the purity was found to be 98%.

(2) After an aqueous solution of cyclopentenone (50 mg/ml) prepared in Example 1-(1) was preserved for 30 days at 4° C., it was analyzed by means of an HPLC according to the following conditions.

Column: Lichrosorb $NH_2$-5 (4.6×250 mm; manufactured by Merck)

Mobile phase: 80% aqueous solution of acetonitrile

Flow rate: 0.8 ml/minute

Column temperature: 25° C.

Detection: Differential refractometer (YRD-880 Midget; manufactured by Shimamura Keiki Seisakusho)

Sample: 100 μl of a 10-fold diluted solution was injected

The result was that, in addition to the peak at 5.7 minutes for cyclopentenone, another peak at 6.8 minutes for hydroxycyclopentanone of the present invention was noted. Its chromatogram is shown in FIG. 1. Thus, FIG. 1 is a graph showing the relation between the retention time and the output of the differential refractometer in which the abscissa indicates a retention time (minutes) while the ordinate indicates an output of the differential refractometer.

Example 2.

(1) Commercially available glucuronolactone (manufactured by Nacalai Tesque) (500 g) was dissolved in 38 liters of water and then steam was blown thereinto so that heating was conducted at 125° C. for five hours. After cooling, the solution was concentrated in vacuo and the concentrate was adjusted to pH 5.0 with NaOH. This was charged in an anion exchange column (20 liters) using a water-equilibrated Diaion SA-10A (manufactured by Mitsubishi Chemical) and eluted with water to give 24 liters of a non-adsorbed fraction.

The fraction was concentrated in vacuo to 2.8 liters, NaCl was added thereto to make the final concentration 2M and the mixture was charged, by two installments, to a column (15 liters) of a synthetic adsorbent SP-207 (manufactured by Mitsubishi Chemical) which was previously equilibrated with a 2M aqueous solution of NaCl. The column was washed with a 2M aqueous solution of NaCl and eluted with a 0.1M aqueous solution of NaCl to give 78 liters of fractions in total.

The total fractions were concentrated in vacuo to 11 liters and the concentrated liquid was subjected to the same SP-207 column chromatography as mentioned above to give 24 liters of eluate. In this case, however, all of the sample was subjected to just one chromatographic operation and the elution was conducted with water.

The eluate was concentrated in vacuo to 100 ml and was desalted by means of electrodialysis using a permeable membrane (AC-110-10; manufactured by Asahi Chemical) to give 100 ml of a solution containing a mixture of cyclopentenone and hydroxycyclopentanone.

(2) The solution (10 ml) containing cyclopentenone and hydroxycyclopentanone obtained in Example 2-(1) was concentrated and evaporated to dryness in vacuo and then dissolved in the upper layer (15 ml) of a mixture of butyl acetate, acetic acid and water (3:2:2). The solution was subjected to the same silica gel column chromatography as in Example 1-(1) to give a fraction containing cyclopentenone which was eluted with 500–700 ml of eluent and a fraction containing hydroxycyclopentanone which was eluted with 950–1700 ml of eluent. Incidentally, the size of the column was 2.5×50 cm. The fraction containing hydroxycyclopentanone was concentrated and evaporated to dryness in vacuo to give 75 mg of hydroxycyclopentanone.

(3) The same silica gel column chromatography as in Example 2-(2) was conducted to give a fraction 1 which was eluted with 1070–1240 ml of eluent and fraction 2 which was eluted with 1320–1500 ml of eluent.

Each of the fractions 1 and 2 was concentrated in vacuo followed by subjecting to an HPLC under the following conditions.

Column: CAPCELL PAK $C_{18}$ SG 300A 5 µm (6×250 mm; manufactured by Shiseido)

Mobile phase: a 0.1% aqueous solution of TFA

Flow rate: 1 ml/minute

Detection: by measuring the absorbance at 210 nm

A peak retention time of which was 6.0 minutes in each of them was collected and freeze-dried. From the HPLC-treated product of the fraction 1 was obtained 20 mg of hydroxycyclopentanone diastereomer A while 27 mg of hydroxycyclopentanone diastereomer B was obtained from the HPLC-treated product of the fraction 2.

Example 3

Hydroxycyclopentanone obtained in Example 2-(2) was dissolved in water to make the concentration 4 mM followed by allowing to stand for 16 hours at 4° C., 37° C. or 45° C. One µl of each of the samples was spotted on a silica gel 60 sheet $F_{254}$ (manufactured by Merck), developed by the upper layer of a mixture of butyl acetate, acetic acid and water (3:2:2) and detected by means of an orcinol-sulfuric acid method. Thus, 400 mg of orcinol monohydrate (manufactured by Nacalai Tesque; 257–30) was dissolved in 22.8 ml of sulfuric acid, water was added to make 200 ml, the solution was sprayed on the thin layer after the development and heated at 120° C. for 1–2 minutes and the resulting spots were observed.

The result was that a spot for cyclopentenone was noted in all of the samples and the higher the temperature for allowing to stand, the stronger the color of the spot for cyclopentenone.

Example 4

(1) NMR

A solution of a mixture of cyclopentenone and hydroxycyclopentanone obtained in Example 2-(1) was evaporated to dryness in vacuo, dissolved in heavy water and $^1$H-NMR spectrum and $^{13}$C-NMR spectrum were measured using a JNM-A500 (manufactured by Nippon Denshi). The result is shown below.

$^1$H-NMR (A)

δ 2.42 (1H, dd, J=2.0, 20.0 Hz, 5-H), 2.53 (1H, dd, J=5.5, 20.0 Hz, 5-H), 3.91 (1H, dd, J=4.0, 10.5, 3-H), 4.23 (1H, dd, J=2.0, 10.5 Hz, 2-H), 4.27 (1H, dd, J=4.0, 5.5 Hz, 4-H)

(B)

δ 2.13 (1H, did, J=9.0, 20.0 Hz, 5-H), 2.86 (1H, ddd, J=2.5, 8.5, 20.0 Hz, 5-H), 3.76 (1H, dd, J=8.5, 10.0, 3-H), 4.04 (1H, dd, J=2.5, 10.0 Hz, 2-H), 4.13 (1H, ddd, J=8.5, 8.5, 9.0 Hz, 4-H)

The chemical shit value of HOD was expressed as 4.65 ppm.

The hydroxycyclopentanone contained in this sample was a mixture of a substance having a structure as shown by the following formula [III] and an enantiomer thereof and a substance having a structure as shown by the following formula [IV] and an enantiomer thereof. One of (A) and (B) shows the signals of the structure of the formula [III] and its enantiomer while another shows the signals of the structure of the formula [IV] and its enantiomer.

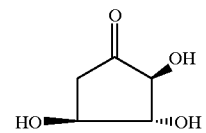

[III]

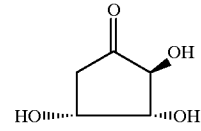

[IV]

Figure 2:
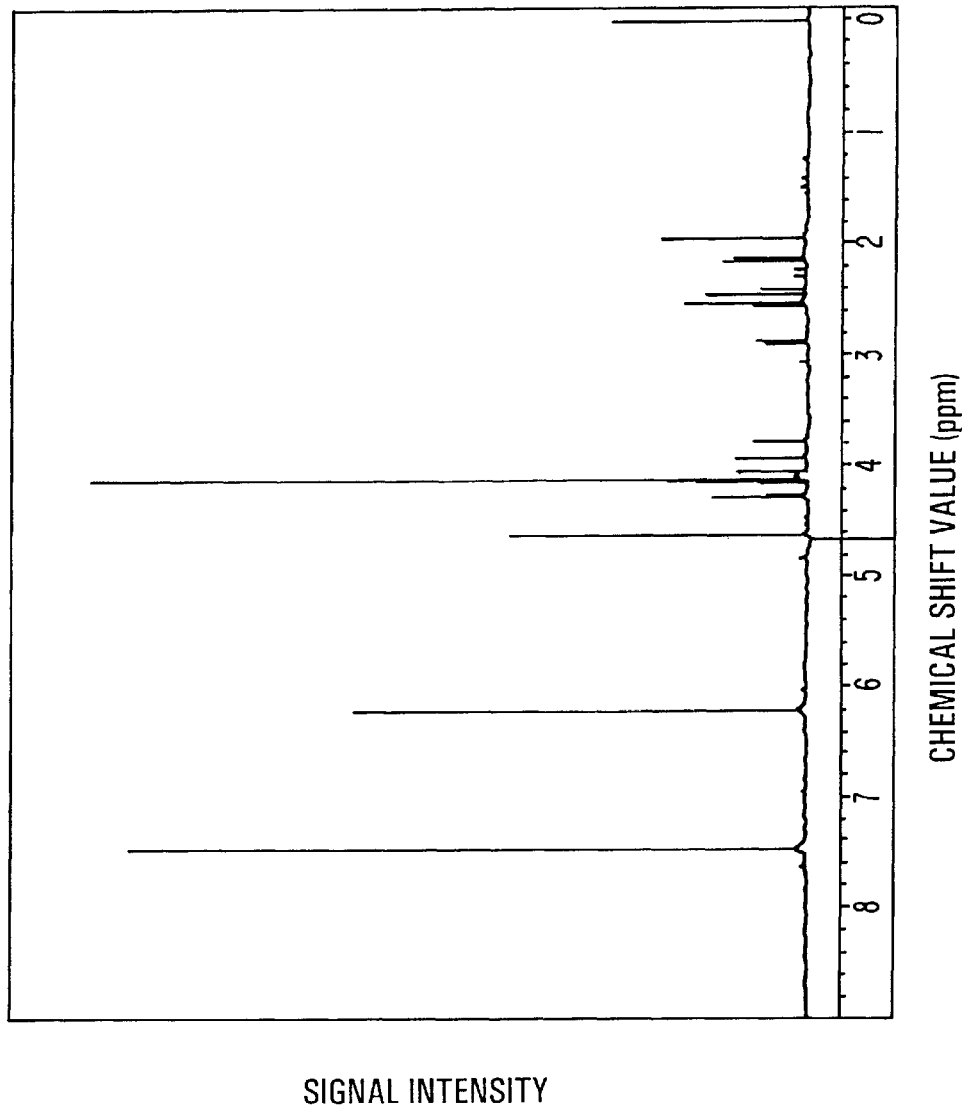
FIG. 2 shows a $^1$H-NMR spectrum of a mixture of cyclopentenone and hydroxycyclopentanone.

The $^1$H-NMR spectrum is shown in FIG. 2. Thus, FIG. 2 shows a $^1$H-NMR spectrum of a mixture of cyclopentenone and hydroxycyclopentanone where an abscissa indicates a chemical shift value (ppm) while an ordinate indicates a signal intensity. Incidentally, the signals of 4.1, 4.6, 6.2 and 7.4 ppm are those derived from cyclopentenone.

$^{13}$C-NMR (A)

δ 44.2 (5-C), 67.4 (4-C), 76.4 (3-C), 78.1 (2-C), 218.1 (1-C)

(B)

δ 43.5 (5-C), 69.5 (4-C), 80.7 (2-C), 80.8 (3-C), 214.7 (1-C)

The chemical shift value of dioxane was expressed as 67.4 ppm.

The hydroxycyclopentanone contained in this sample was a mixture of a substance having a structure as shown by the formula [III] and an enantiomer thereof and a substance having a structure as shown by the formula [IV] and an enantiomer thereof. One of (A) and (B) shows the signals of the structure of the formula [III] and its enantiomer while another shows the signals of the structure of the formula [IV] and its enantiomer.

Figure 3:
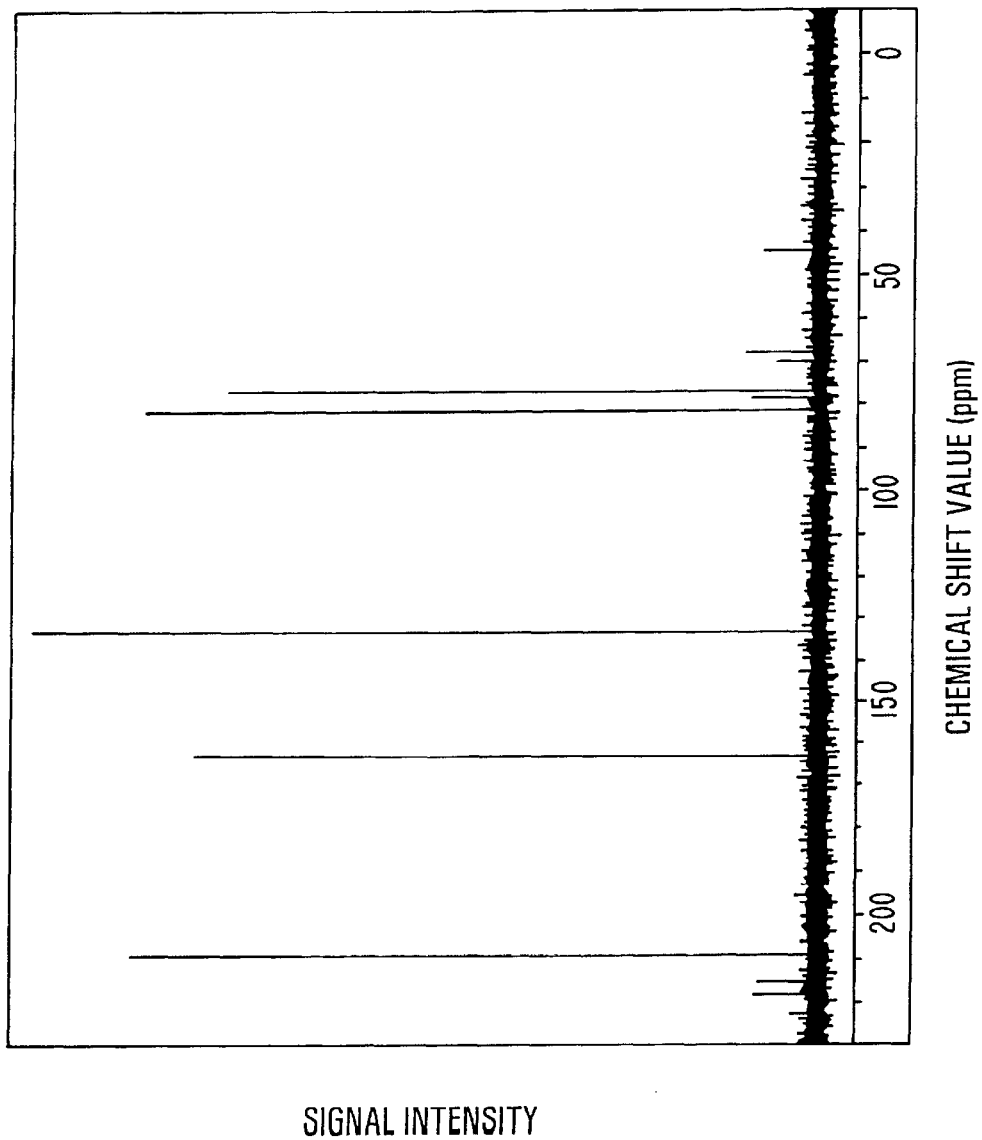
FIG. 3 shows a $^{13}$C-NMR spectrum of a mixture of cyclopentenone and hydroxycyclopentanone.

The $^{13}$C-NMR spectrum is shown in FIG. 3. Thus, FIG. 3 shows a $^{13}$C-NMR spectrum of a mixture of cyclopentenone and hydroxycyclopentanone where an abscissa indicates a chemical shift value (ppm) while an ordinate indicates a signal intensity. Incidentally, the signals of 76.9, 81.4, 132.9, 163.2 and 208.0 ppm are those derived from cyclopentenone.

(2) GC/MS

A solution (0.5 μl) containing a mixture of cyclopentenone and hydroxycyclopentanone obtained in Example 2-(1) was evaporated to dryness in vacuo, dissolved in 100 μl of a 4:1:4 mixture of trimethylchlorosilane (manufactured by GL Science), N,O-bis(trimethylsilyl)-acetamide (manufactured by GL Science) and anhydrous pyridine (a silylation grade; manufactured by Pierce) and trimethylsilylated at 60° C. for one hour. This sample (1 μl) was analyzed by means of gas chromatography/mass analysis (GC/MS) as mentioned below.

Column: TC-1 (30 m×0.25 mm; manufactured by GL Science)
Column temperature: 100° C.→160° C. (4° C./minute)
160° C.→300° C. (16° C./minute)
300° C. (5 minutes)
Carrier gas: Helium (1.2 ml/minute)

Figure 4:
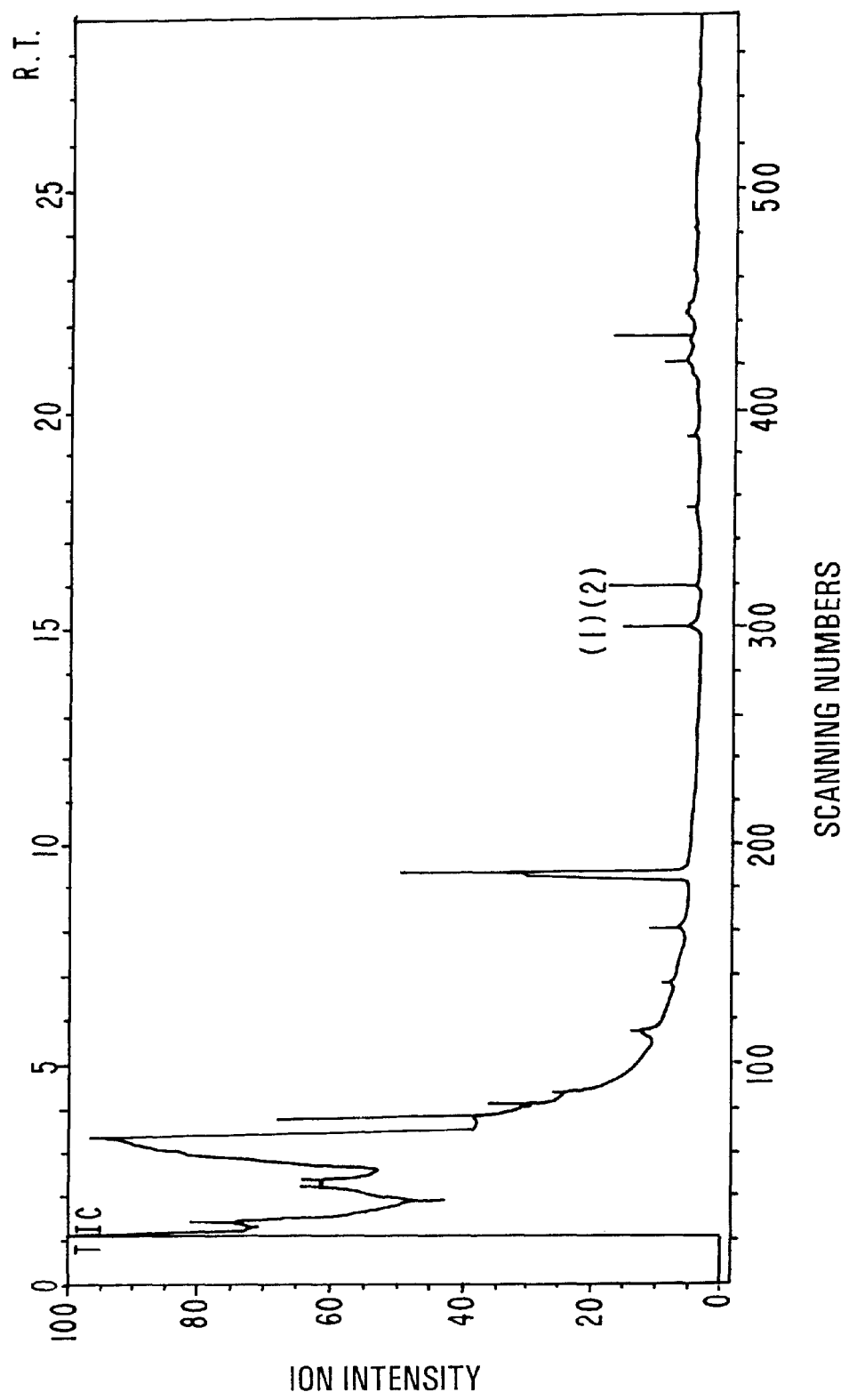
FIG. 4 shows a gas chromatogram of a mixture of trimethylsilylated cyclopentenone and hydroxycyclopentanone.
Figure 5:
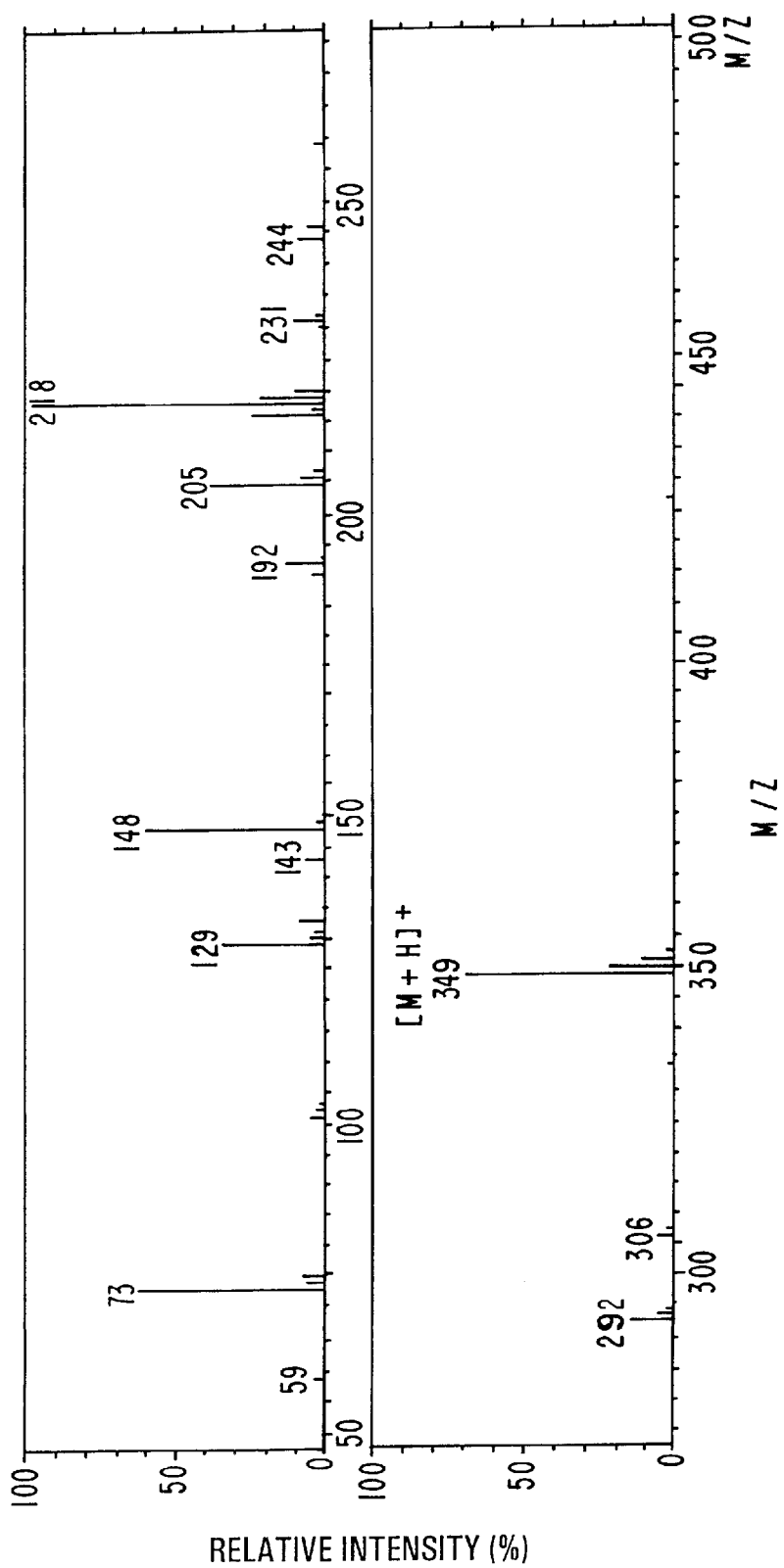
FIG. 5 shows a mass spectrum of the peak (1) of FIG. 4.
Figure 6:
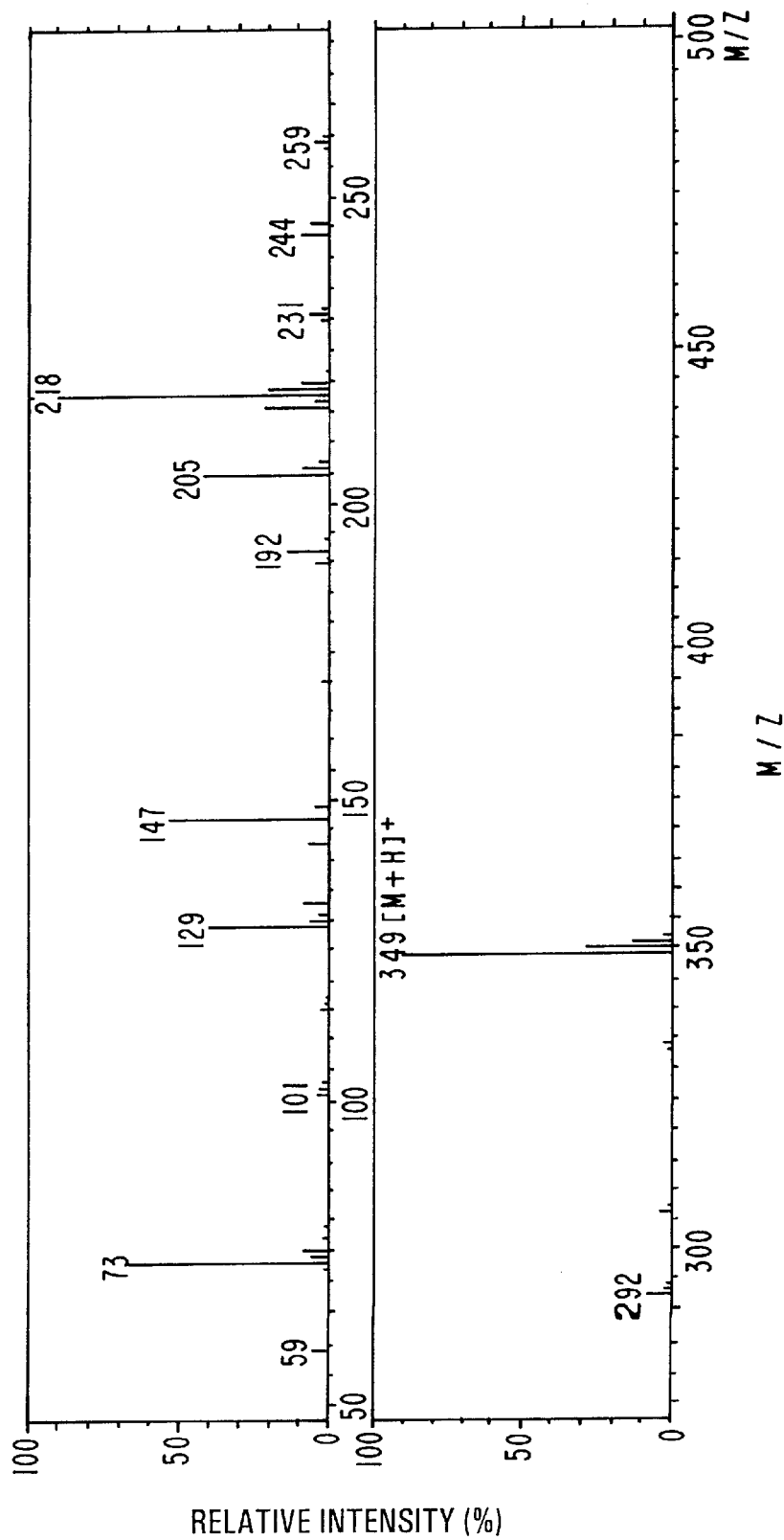
FIG. 6 shows a mass spectrum of the peak (2) of FIG. 4.

The result is given in FIG. 4, FIG. 5 and FIG. 6. Thus, FIG. 4 shows a gas chromatogram of a mixture of trimethylsilylated cyclopentenone and hydroxycyclopentanone in which an abscissa indicates a scanning number while an ordinate indicates an ion intensity. FIG. 5 and FIG. 6 show mass spectra of the peak (1) and the peak (2) in FIG. 4 where an abscissa indicates M/Z while an ordinate indicates a relative intensity (%).

As a result, both peak (1) and peak (2) of FIG. 4 showed an M/Z of 349 [M+H]$^+$ and agreed with the values calculated from the stricture of trimethylsilylated hydroxycyclopentanone.

Example 5.

(1) NMR

Each of hydroxycyclopentanone diastereomers A and B obtained in Example 2-(3) was dissolved in heavy water and $^1$H-NMR spectrum and $^{13}$C-NMR spectrum were measured using a JNM-A500 (manufactured by Nippon Denshi). The results are as follows.

$^1$H-NMR
Hydroxycyclopentanone diastereomer A
δ 2.42 (1H, dd, J=2.0, 20.0 Hz, 5-H), 2.53 (1H, dd, J=5.5, 20.0 Hz, 5-H), 3.91 (1H, dd, J=4.0, 10.5, 3-H), 4.23 (1H, dd, J=2.0, 10.5 Hz, 2-H), 4.27 (1H, dd, J=4.0, 5.5 Hz, 4-H)
Hydroxycyclopentanone diastereomer B
δ 2.13 (1H, dd, J=9.0, 20.0 Hz, 5-H), 2.86 (1H, ddd, J=2.5, 8.5, 20.0 Hz, 5-H), 3.76 (1H, dd, J=8.5, 10.0, 3-H), 4.04 (1H, dd, J=2.5, 10.0 Hz, 2-H), 4.13 (1H, ddd, J=8.5, 8.5, 9.0 Hz, 4-H)

The chemical shift value of HOD was expressed as 4.65 ppm.

One of hydroxycyclopentanone diastereomers A and B is a substance having a structure as shown by the formula [III] and an enantiomer thereof and another is a substance having a structure as shown by the formula [IV] and an enantiomer thereof.

Figure 7:
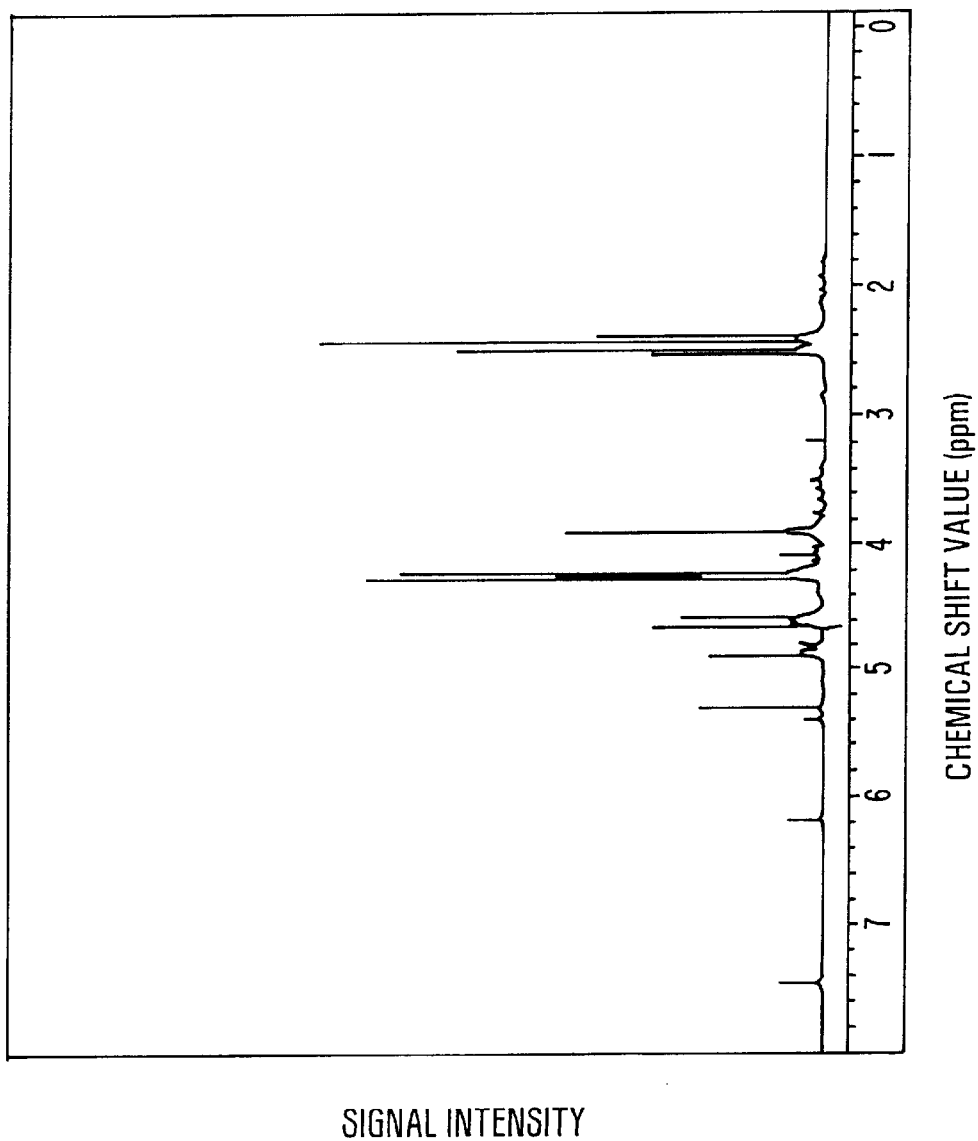
FIG. 7 shows a $^1$H-NMR spectrum of hydroxycyclopentanone diastereomer A.
Figure 8:
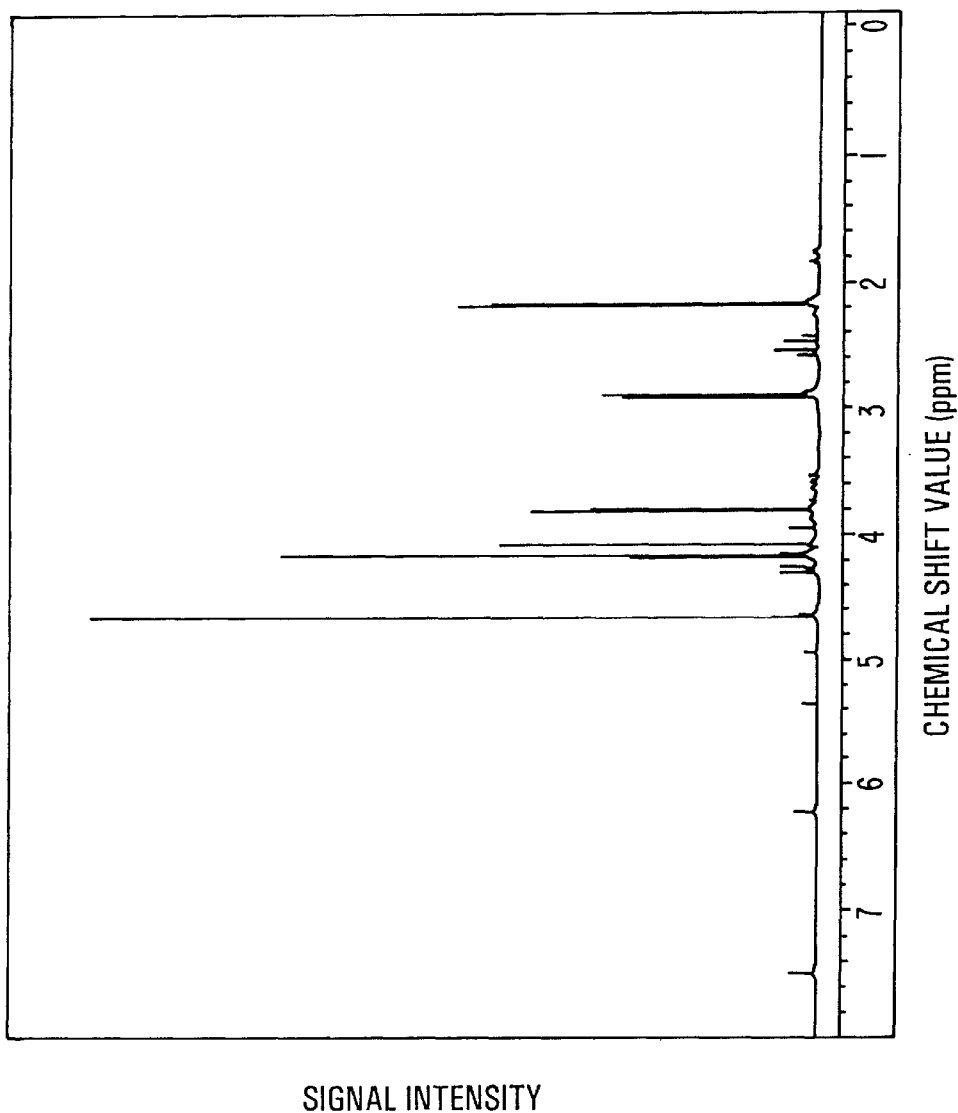
FIG. 8 shows a $^1$H-NMR spectrum of hydroxycyclopentanone diastereomer B.

FIG. 7 and FIG. 8 show $^1$H-NMR spectra. Thus, FIG. 7 shows a $^1$H-NMR spectrum of hydroxycyclopentanone diastereomer A while FIG. 8 shows a $^1$H-NMR spectrum of hydroxycyclopentanone diastereomer B in which an abscissa indicates a chemical shift value (ppm) while an ordinate indicates a signal intensity.

$^{13}$C-NMR
Hydroxycyclopentanone diastereomer A
δ 44.2 (5-C), 67.4 (4-C), 76.4 (3-C), 78.1 (2-C), 218.1 (1-C)
Hydroxycyclopentanone diastereomer B
δ 43.5 (5-C), 69.5 (4-C), 80.7 (2-C), 80.8 (3-C), 214.7 (1-C)

The chemical shift value of dioxane was expressed as 67.4 ppm.

One of hydroxycyclopentanone diastereomers A and B is a substance having a structure of the formula [III] and its enantiomer while another is a substance having a structure of the formula [IV] and its enantiomer.

Figure 9:
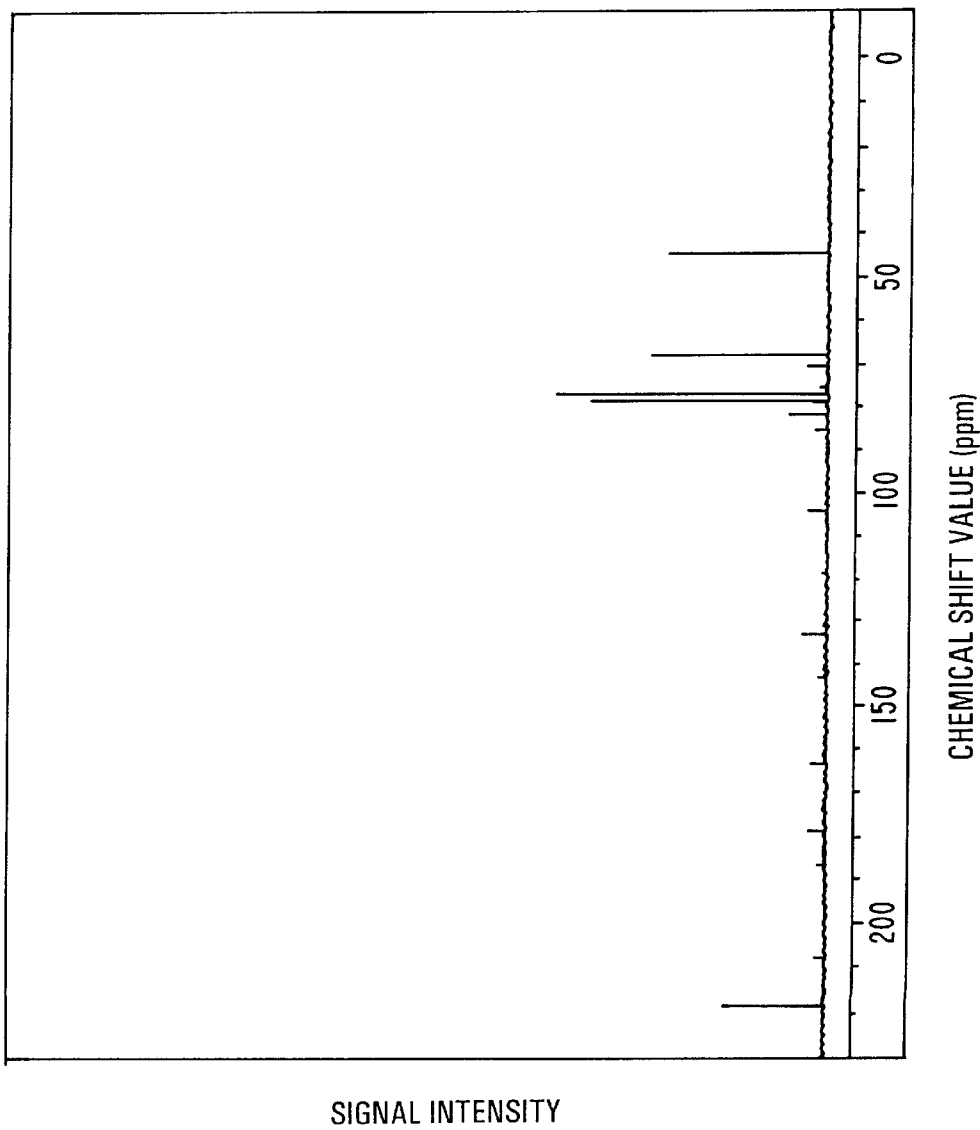
FIG. 9 shows a $^{13}$C-NMR spectrum of hydroxycyclopentanone diastereomer A.
Figure 10:
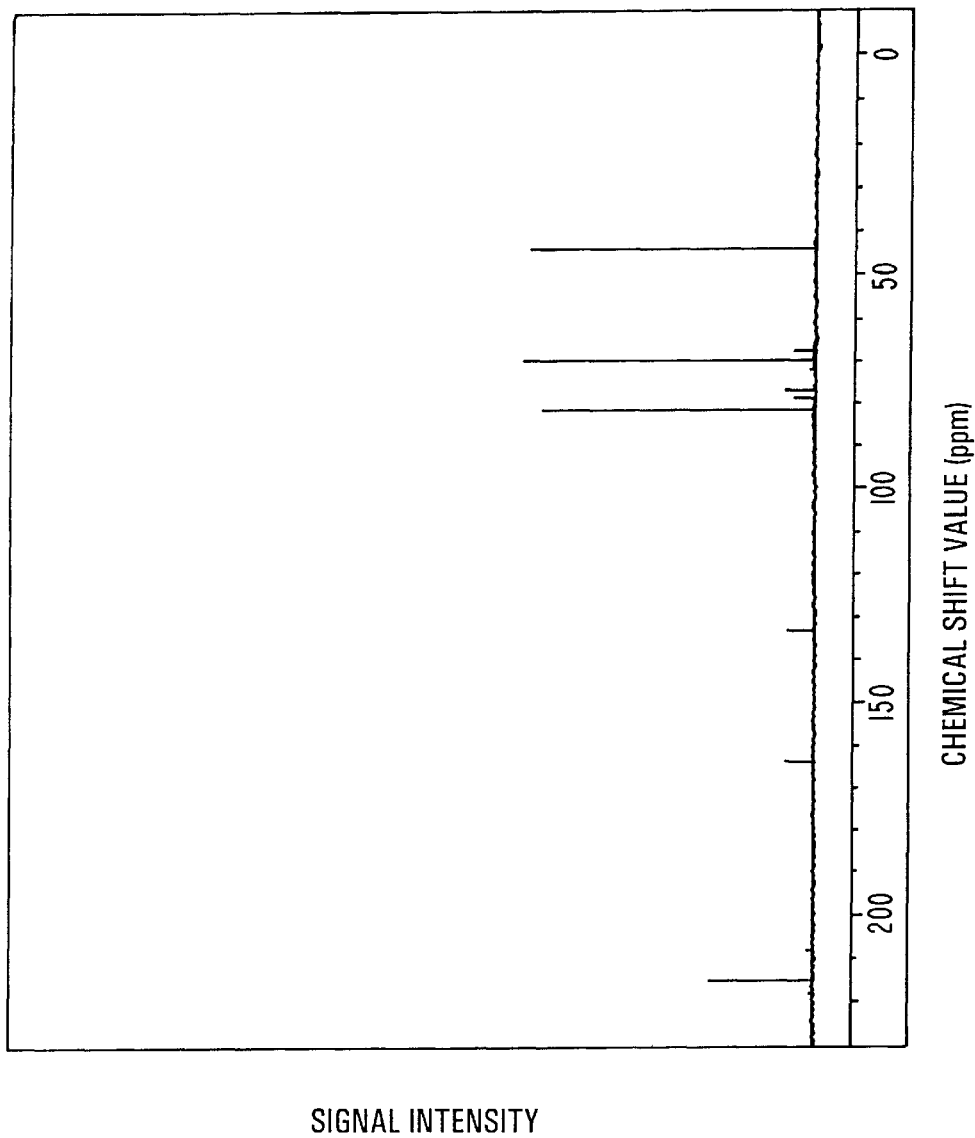
FIG. 10 shows a $^{13}$C-NMR spectrum of hydroxycyclopentanone diastereomer B.

The $^{13}$C-NMR spectra are shown in FIG. 9 and FIG. 10. Thus, FIG. 9 shows a $^{13}$C-NMR spectrum of hydroxycyclopentanone diastereomer A while FIG. 10 shows that of hydroxycyclopentanone diastereomer B where an abscissa indicates a chemical shift value (ppm) while an ordinate indicates a signal intensity.

(2) GC/MS

Each 0.5 μl of a 20 mM aqueous solution of hydroxycyclopentanone diastereomer A and a 40 mM aqueous solution of hydroxycyclopentanone diastereomer B obtained in Example 2-(3) was evaporated to dryness in vacuo, dissolved in 100 μl of a 4:1:4 mixture of trimethylchlorosilane (manufactured by GL Science), N,O-bis(trimethylsilyl)—acetamide (manufactured by GL Science) and anhydrous pyridine (silylation grade; manufactured by Pierce) and trimethylsilylated at room temperature for 20 minutes. This sample (2 μl) was analyzed by means of gas chromatography/mass analysis (GC/MS) as mentioned below.

Column: TC-1 (30 m×0.25 mm; manufactured by GL Science)
Column temperature: 100° C.→160° C. (4° C./minute)
160° C.→300° C. (16° C./minute)
300° C. (5 minutes)
Carrier gas: Helium (1.2 ml/minute)

Figure 11:
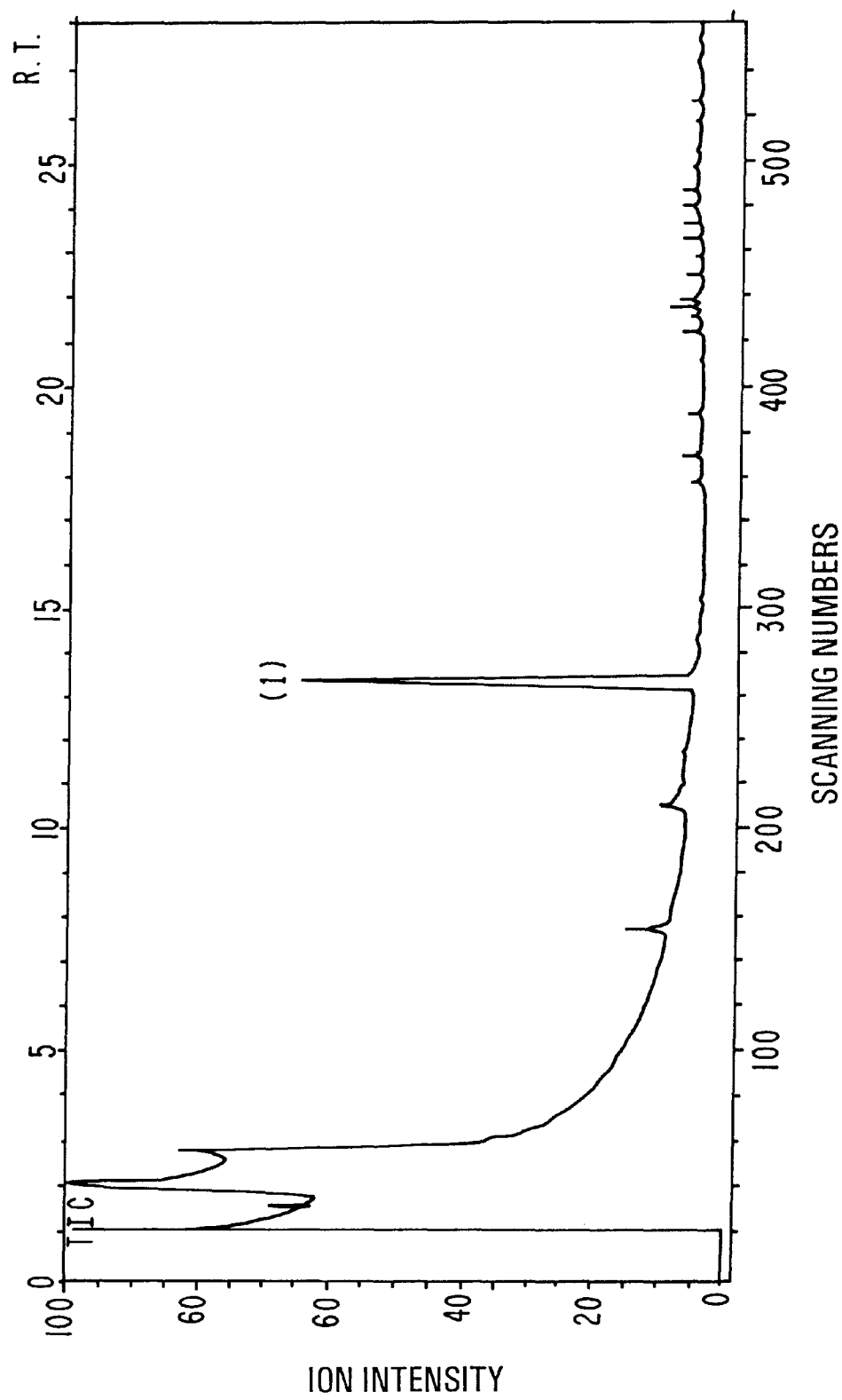
FIG. 11 shows a gas chromatogram of trimethylsilylated hydroxycyclopentanone diastereomer A.
Figure 12:
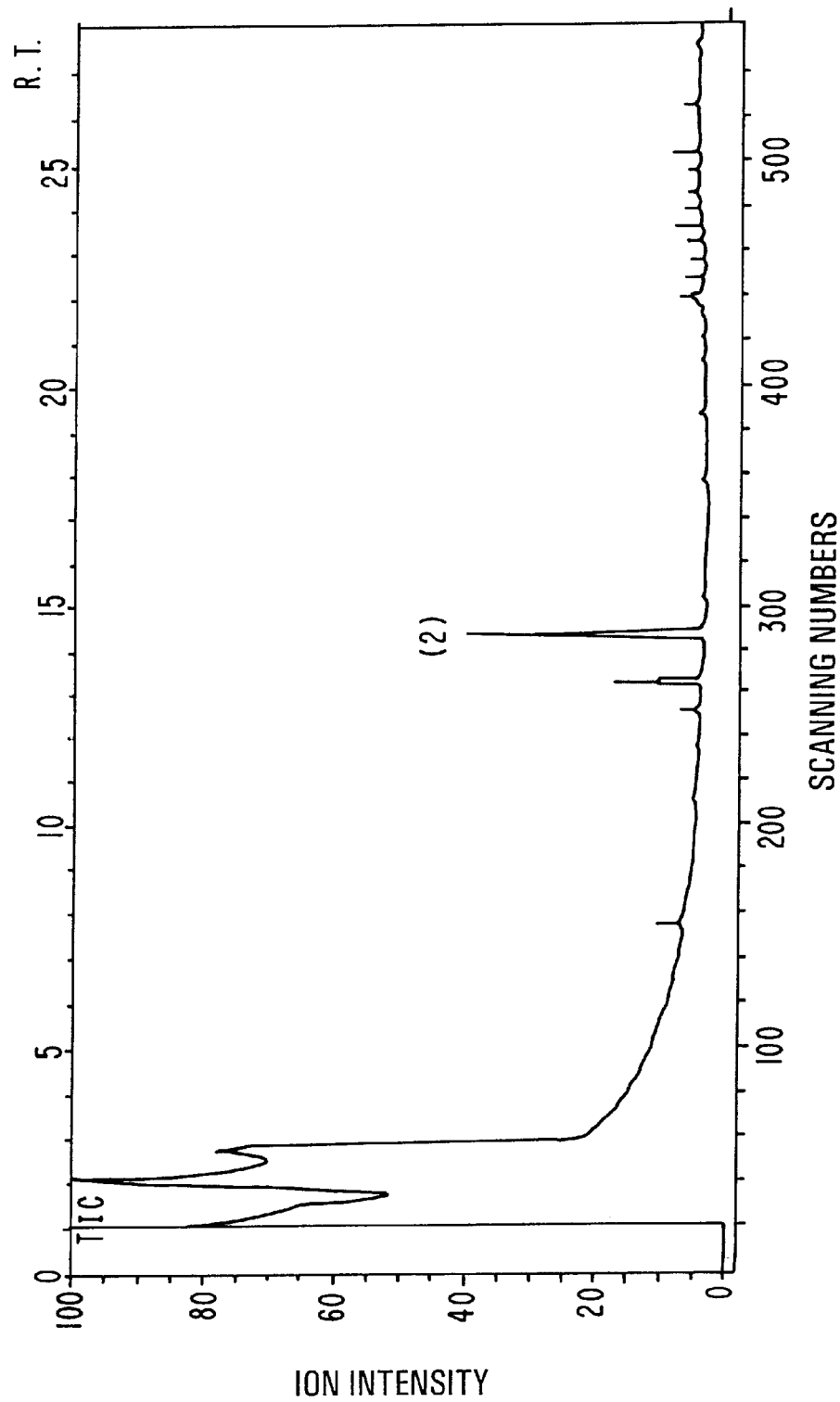
FIG. 12 shows a gas chromatogram of trimethylsilylated hydroxycyclopentanone diastereomer B.
Figure 13:
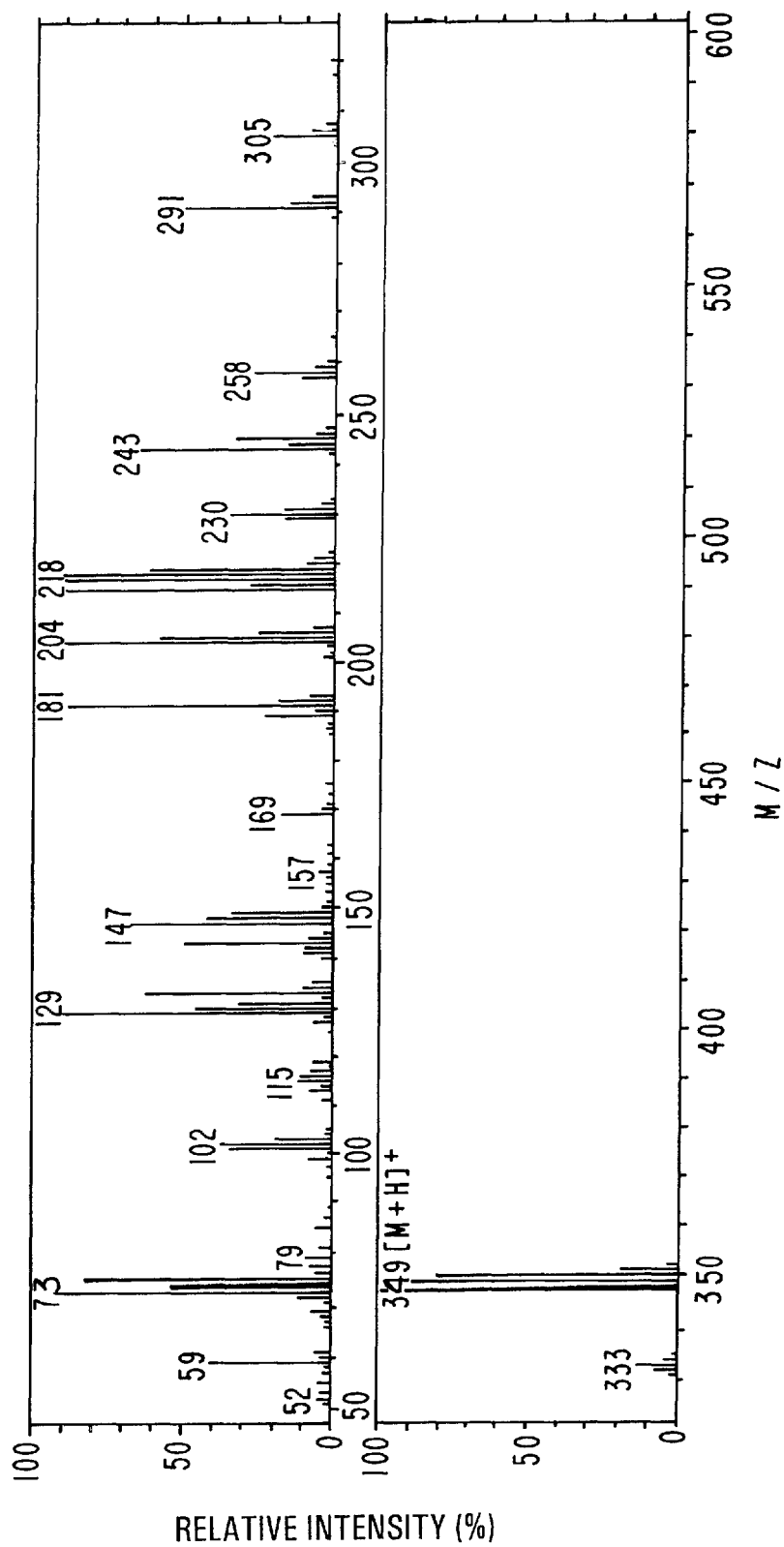
FIG. 13 shows a mass spectrum of the peak (1) of FIG. 11.
Figure 14:
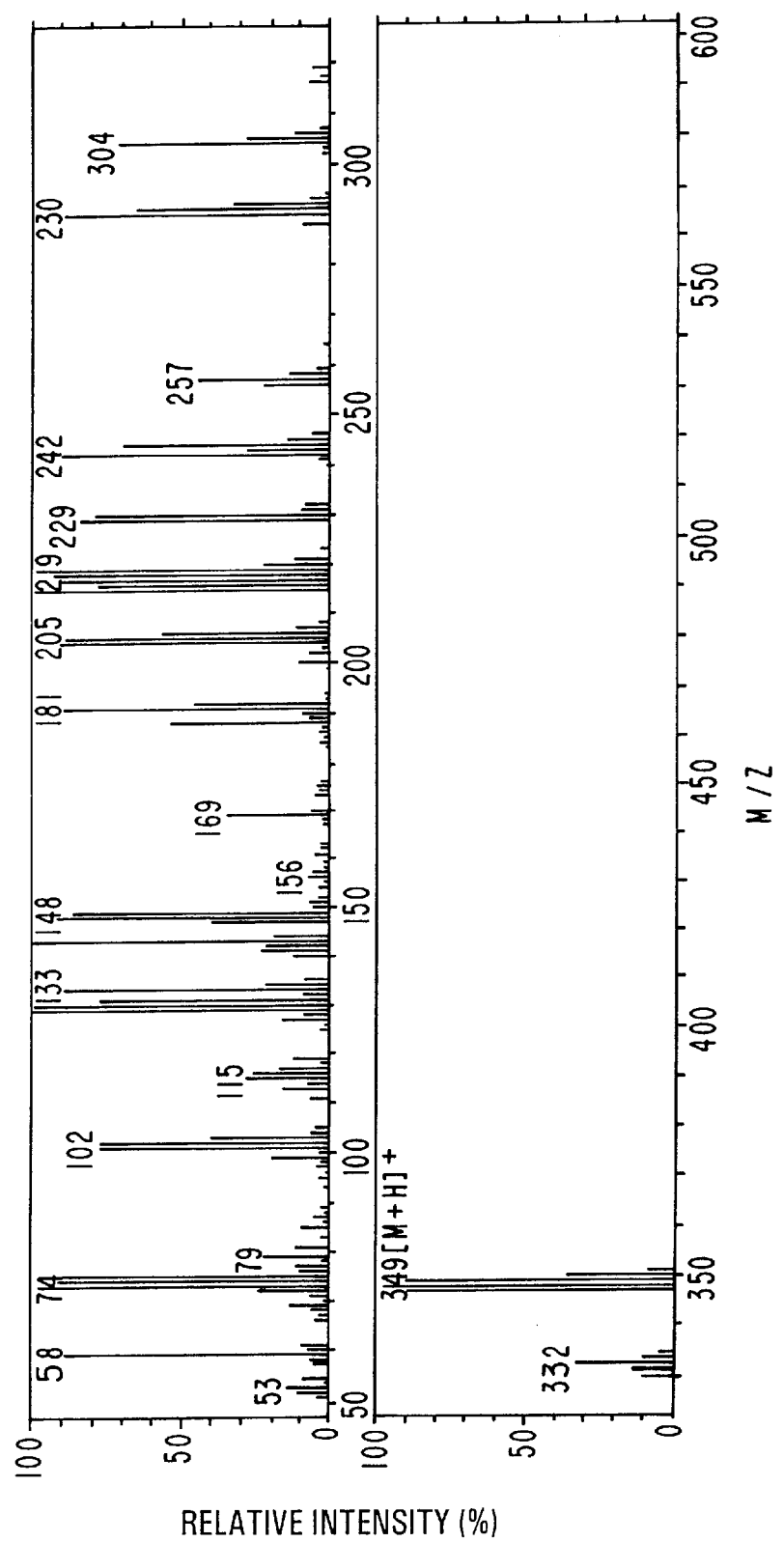
FIG. 14 shows a mass spectrum of the peak (2) of FIG. 12.

The result is given in FIG. 11 to FIG. 14. Thus, FIG. 11 shows a gas chromatogram of trimethylsilylated hydroxycyclopentanone diastereomer A and FIG. 12 is a gas chromatogram of trimethylsilylated hydroxycyclopentanone diastereomer B in which an abscissa indicates a scanning number while an ordinate indicates an ion intensity. FIG. 13 and FIG. 14 show mass spectra of the peak (1) of FIG. 11 and the peak (2) of FIG. 12, respectively where an abscissa indicates M/Z while an ordinate indicates a relative intensity (%)

As a result, both peak (1) of FIG. 11 and peak (2) of FIG. 12 showed M/Z of 349 [M+H]$^+$ and agreed with the values calculated from the structure of trimethylsilylated hydroxycyclopentanone.

Example 6.

(1) Each 10 μl of a 150, 110, 70 or 40 μM aqueous solution of hydroxycyclopentanone diastereomer A, a 200, 150, 100 or 60 μM aqueous solution of hydroxycyclopentanone diastereomer B or water as a control was added to each well of a 96-well microtiter plate. Promyelocytic leukemia cells strain HL-60 (ATCC CCL-240) were suspended in an RPMI 1640 medium containing 10% of fetal calf serum to an extent of $5 \times 10^4$ cells/ml and each 90 μl thereof was pipetted into each well of the above-mentioned microtiter plate and incubated at 37° C. for 48 hours in the presence of 5% of $CO_2$. The incubation was continued for four hours more after addition of 10 μl of a phosphate-buffered saline solution containing 5 mg/ml of 3-(4,5-dimethylthiazol-2-yl)-2, 5-diphenyltetrazolium bromide (MTT; manufactured by Sigma) thereto and then the state of growth of the cells was observed under a microscope. Further, 100 μl of 2-propanol containing 0.04N HCl was added thereto followed by well stirring and then the absorbance at 590 nm was measured.

The result was that growth of the cells was not noted in a section to which 110 μM or more hydroxycyclopentanone diastereomer A was added (final concentration: 11 μM) and in a section to which 100 μM or more hydroxycyclopentanone diastereomer B was added (final concentration: 10 μM). Accordingly, it is now apparent that hydroxycyclopentanone diastereomer A and hydroxycyclopentanone diastereomer B completely inhibited the growth of the HL-60 cells at the concentrations of 11 μM and 10 μM, respectively.

MERIT OF THE INVENTION

The present invention offers hydroxycyclopentanone, its optically active substance or salt thereof having a high safety which shows physiological activities such as anticancer action, action of suppressing the cancer cell growth, action of inducing the cancer cell differentiation, apoptosis-inducing action, antibacterial action, antiviral action and action of improving the hepatic function. The present invention also offers pharmaceutical agent, food and beverage containing said compound having such physiologically active functions.

In accordance with the present invention, it is now possible to easily and efficiently manufacture hydroxycyclopentanone, its optically active substance or salt thereof starting from the substances which are derived from nature.

Due to various physiological activities of hydroxycyclopentanone, its optically active substance or salt thereof offered by the present invention such as anticancer action, antibacterial action, apoptosis inducing action, antiviral action and action of improving the hepatic function, it is now possible to use said compound as a pharmaceutical agent having effect of prevention of carcinogenesis, effect of suppression of cancer, effect of prevention and therapy of viral diseases, effect of prevention of Alzheimer's disease and effect of improvement of hepatic functions and said pharmaceutical agent is useful for maintenance of homeostasis of living body, particularly for keeping the good health of stomach and intestine.

In addition, it is now possible in accordance with the present invention that an appropriate amount of a physiologically active hydroxycyclopentanone, its optically active substance or salt thereof is/are contained in food or beverage. Due to various physiological activites of hydroxycyclopentanone, its optically active substance or salt thereof such as anticancer action, differentiation inducing action, action of suppressing the growth of abnormal cells, apoptosis-inducing action, antiviral action, antibacterial action and action of improving the hepatic function, the food or beverage offered by the present invention is a healthy food or beverage having a function of keeping the homeostasis of living organism such as effect of prevention of carcinogenesis, anticancer effect, effect of prevention of viral diseases, antibacterial effect and apoptosis-inducing effect and, in accordance with the present invention, food or beverage containing a functional substance useful for keeping the health of stomach and intestine can be offered. Further, as a result of addition of hydroxycyclopentanone, its optically active substance or salt thereof, the antibacterial action of food or beverage can be easily enhanced and the agents containing hydroxycyclopentanone, its optically active substance or salt thereof are quite useful as antiseptic agents for food or beverage.

What is claimed is:

1. 2,3,4-trihydroxycyclopentanone represented by the following formula [I], its optically active isomer or salt thereof.

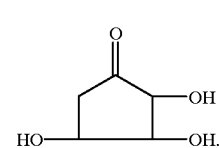

[I]

2. A method of manufacturing 2,3,4-trihydroxycyclopentanone, its optically active isomer or salt thereof comprising the following steps:

(A): a step wherein at least one substance selected from the following (a), (b) and (c) is heated to produce 2,3,4-trihydroxycyclopentanone; wherein
 (a): uronic acid or uronic acid derivative(s),
 (b): a saccharide compound which contains uronic acid and/or uronic acid derivative(s), and
 (c): a substance containing a saccharide compound which contains uronic acid and/or uronic acid derivative(s);

(B): an optional step wherein 2,3,4-trihydroxycyclopentanone is isolated from the resulting heat-treated product.

3. The method according to claim 2 wherein uronic acid is galacturonic acid, glucuronic acid, guluronic acid, mannuronic acid and/or iduronic acid.

4. The method according to claim 2 wherein uronic acid derivative is salt of uronic acid, or uronic acid lactone, uronic acid ester, uronic acid amide or salt thereof.

5. The method according to claim 2 wherein the saccharide compound is a saccharide compound which is selected from pectin, pectic acid, alginic acid, hyaluronic acid, heparin, fucoidan, chondroitin sulfate, chondroitin, dermatan sulfate and/or decomposed product thereof, wherein the decomposed product is obtained by chemical, enzymatic or physical treatment of the saccharide compound.

6. A method of manufacturing according to any of claims 2–5 wherein the heat-treated product is a heat-treated product which is obtained by heating at 60–350° C. for several seconds to several days.

7. The method of manufacturing according to any of claims 2–5 wherein the heat-treated product is a heat-treated product which is obtained by heating under acidic to neutral conditions.

8. A method of manufacturing 2,3,4-trihydroxycyclopentanone represented by the formula [I], its optically active isomer or salt thereof comprising a step where 4,5-dihydroxy-2-cyclopenten-1-one represented by the following formula [II] is converted to 2,3,4-trihydroxycyclopentanone represented by the following formula [I]

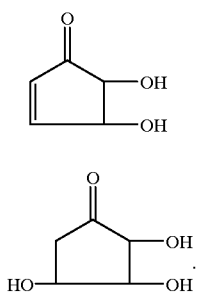

9. A pharmaceutical agent containing at least one compound selected from 2,3,4-trihydroxycyclopentanone, its optically active isomer or salt thereof according to claim 1.

10. The pharmaceutical agent according to claim 9 wherein the agent is an anticancer agent.

11. Food or beverage additionally containing at least one compound selected from 2,3,4-trihydroxycyclopentanone, its optically active substance or salt thereof according to claim 1.

12. The method according to claim 6, wherein the heat-treated product is a heat-treated product which is obtained by heating under acidic to neutral conditions.

* * * * *